United States Patent
Roemer et al.

(10) Patent No.: US 10,364,447 B2
(45) Date of Patent: Jul. 30, 2019

(54) PRODUCTION OF OMEGA-3 FATTY ACIDS BY MYXOBACTERIA

(75) Inventors: Ernst Roemer, Bucha (DE); Rolf Müller, Blieskastel (DE); Ronald O. Garcia, Saarbrücken (DE); Mark Stadler, Niederkirchen (DE); Dominik Pistorius, Saarbrücken (DE); Alexander Brachmann, Saarbrücken (DE)

(73) Assignee: Universitat Des Saarlandes, Saarbrucken (DE)

( * ) Notice: Subject to any disclaimer, the term of this patent is extended or adjusted under 35 U.S.C. 154(b) by 776 days.

(21) Appl. No.: 13/132,052

(22) PCT Filed: Dec. 1, 2009

(86) PCT No.: PCT/EP2009/008560
§ 371 (c)(1),
(2), (4) Date: Jul. 15, 2011

(87) PCT Pub. No.: WO2010/063451
PCT Pub. Date: Jun. 10, 2010

(65) Prior Publication Data
US 2011/0275846 A1    Nov. 10, 2011

(30) Foreign Application Priority Data
Dec. 1, 2008 (EP) .................... 08170390

(51) Int. Cl.
*C12P 7/64* (2006.01)
*C12R 1/01* (2006.01)

(52) U.S. Cl.
CPC ............. *C12P 7/6427* (2013.01); *C12R 1/01* (2013.01)

(58) Field of Classification Search
CPC ............. C12P 7/6427; C12P 1/04; C12R 1/01
USPC ................................... 435/134, 170
See application file for complete search history.

(56) References Cited

U.S. PATENT DOCUMENTS

| | | |
|---|---|---|
| 7,022,512 B2 | 4/2006 | Barclay |
| 2004/0203121 A1 | 10/2004 | Barclay |
| 2006/0099694 A1 | 5/2006 | Tremblay et al. |
| 2013/0196391 A1 | 8/2013 | Wenzel et al. |

FOREIGN PATENT DOCUMENTS

| | | |
|---|---|---|
| JP | 2006-513713 A | 4/2006 |
| WO | 2004/083442 A2 | 9/2004 |
| WO | WO 2007-068997 | 6/2007 |
| WO | 2011/151298 A1 | 12/2011 |

OTHER PUBLICATIONS

Zhang et al., 2003, Letters in Applied Microbiology, 34, 178-181.*
Yamanaka et al., 1987, J. Gen. Appl. Microbiol., 33, 247-265.*
Dickschat, J.S. et al. "Biosynthesis of iso-fatty acids in myxobacteria," Organic & Biomolecular Chemistry, vol. 3, No. 15, Aug. 7, 2005, pp. 2824-2831.
Dickschat, J.S. et al.: "Supplementary Information for: Biosynthesis of iso-fatty acids in myxobacteria," Organic & Biomolecular Chemistry, [online] 2005, XP002527448, retrieved from the internet: http://rsc.org/suppdata/0B/b5/b504889c/b504889c.pdf [retrieved on May 12, 2009].
Iizuka, t. et al., "*Plesiocystis pacifica* gen. nov. sp. nov., a marine myxobacterium that contains dehydrogenated menaquinone, isolated from the Pacific coasts of Japan," International Journal of Systematic and Evolutionary Microbiology, vol. 53, 2003, pp. 189-195.
Izuka et al, "Supplementary data for: *Plesiocystis pacifica* gen. nov., sp. Nov., a marine myxobacterium that contains dehydrogenated menaquinone, isolated from the Pacific coasts of Japan,", Internaitnoal Journal of Systematic and Evolution ary Microbiology, [online] 2003, XP002527449, retrieved from the Internet: http://ijs.sqmjournals.org/cgi/data/53/1/189/DC1/1> [retrieved on May 12, 2009].
Reichenbach, H. et al. "*Byssophaga cruenta* partial 16S rRNA gene, strain DSM 14553T," XP002527450, Database Embl (online), Oct. 2, 2006, database accession No. AH833647.
Aki, Tsunehiro, et. al., "Lipid Composition of a Newly Isolated Polyunsaturated Fatty Acid-Producing Fungus", *Journal of Fermentation and Bioengineering*, vol. 86, No. 5, 1998.
Amann, Rudolf, I., "Phylogenetic Identification and In Situ Detection of Individual Microbial Cells without Cultivation", *Microbiological Reviews*, vol. 59, No. 1, 1995.
Athalye, Sneha, et al., "Use of Biodiesel-Derived Crude Glycerol for Producing Eicosapentaenoic Acid (EPA) by the Fungus *Pythium irregular*", J. Agric. Food Chem., 57, 2009.
Cheng, Ming, et. al., "Fungal Production of eicosapentaenoic and archidonic acids from industrial waste streams and crude soybean oil", *Bioresource Technology*, 67, 1999.
Garcia, Ronald O., et. al., "*Phaselicyslis flava* gem Nov., sp. nov., an arachidonic acid-containing soil myxobacterium, and the description of Phaselicycstidaceae fam. nov.", *International Journal of Systematic and Evolutionary Microbiology*, 59, 2009.
Gentile, G., et. al., *Shewanella* sp. GA-22, a psychrophilic hydrocarbonoclastic antarctic bacterium producing polyunsaturated fatty acids, *Journal of Applied Microbiology*, 95, 2003.
Hinzpeter, I., et. al., "Alternativas biotenológicas para la producción de ácidos grasos pollinsasturados omega-3" Grasas y Aceites, 57, Jul.-Sep. 2006.
Iizuka, Takashi, et. al., "*Enhygromyxa salina* gen. nov., sp. nov., a Slightly Halophilic Myxobacteriu Isolated from the Coastal Areas of Japan", *System. Appl. Microbiol.*, 26. 2003.

(Continued)

*Primary Examiner* — Sharmila G Landau
*Assistant Examiner* — Paul C Martin
(74) *Attorney, Agent, or Firm* — Seed IP Law Group LLP

(57) ABSTRACT

The present invention provides a method for producing ω-3 polyunsaturated fatty acids by culturing specific myxobacterial stains and myxobacterial strains suitable for said method.

10 Claims, 10 Drawing Sheets
Specification includes a Sequence Listing.

(56) References Cited

OTHER PUBLICATIONS

Metz, James G., et. al., "Production of Polyunsaturated Fatty Acids by Polyketide Sythases in Both Prokaryotes and Eukaryotes", *Science*, vol. 293, Jul. 13, 2001.
Nichols, David, et. al., "Developments with Antarctic microorganisms: culture collections, bioactivity screening, taxonomy, PUFA production and cold-adapted enzymes", *Current Opinion in Biotechnology*, vol. 10, Issue 3, Jun. 1999.
Reichenbach, Hans et. al., "The Myxobacteria, The Prokaryotes: A Handbook on the Biology of Bacteria: vol. 7" *The Prokaryotes: A Handbook on the Biology of Bacteria*, vol. 7, 2006.
Reichenbach, Hans, et. al., "*Byssovaorax cruenta* gen. nov., sp. nov, nom. rev., a cellulose-degrading myxobacterium: rediscovery of *Myrococcu crentus*", *International Journal of Systematic and Evolutionary Microbiology*, 2006, 56.
Reichenbach, Hans, et. al., "Order VIII. Myxococcales, Bergey's Manual of Systematic Bacteriology Second Edition", *Bergey's Manual of Systematic Bacteriology, vol. Two, The Proteobacteria Part C, The Alpha-, Beta-, Delta-, and Epsilonproteobacteria*, Department of Microbiology and Molecular Genetics, Michigan State University, East Lansing Michigan, USA, 2005.
Sproer, Cathrin, et al., "The correlation between morphological and phylogenetic classification of myxobacteria", *International Journal of Systematic Bacteriology*, 49, 1999.
Teale, M,C., et. al., *Omega 3 Fatty Acid Research*, Nova Science Publishers, Inc., New York, 2006.
Tornabene, Thomas G., et. al., "Lipid Analysis and the Relationship to Chemotaxonomy", *Methods in Microbiology*, vol. 18, 1985.
Torsvik, Vigdis, et. al., "High Diversity in DNA of Soil Bacteria", *Applied and Environmental Microbiology*, vol. 56, No. 3, Mar. 1990.
Velicer, Gregory, J., et. al., "Why Cooperate? The Ecology and Evolution of Myxobacteria", *Myxobacteria: Multicellularity and Differentiation*, ASM Press, Washington, D.C., 2008.
Ward, Owen P., et. al., "Omega-3-6 fatty acids" Alternative sources of production, *Process Biochemistry*, 40, 2005.
Weisburg, William G., et. al., "16S Ribosomal DNA Amplification for Phylogenetic Study", *Journal of Bacteriology*, vol. 173, No. 2, Jan. 1991.
Wu, Zhi-Hong, et. al., "Exploring the diversity of myxobacteria in a soil niche by myxobacteria-specific primers and probe", *Environmental Microbiology*, vol. 7, No. 10, 2005.
Iizuka et al., "*Enhygromyxa salina* gen. nov., sp. nov., a Slightly Halophilic Myxobacterium Isolated from the Coastal Areas of Japan," *System. Appl. Microbiol.* 26:189-196, 2003.
Japanese Office Action with English Translation dated Jul. 7, 2014, for corresponding JP Application No. 2011-537901, 11 pages.

* cited by examiner cont. of Figure 3:
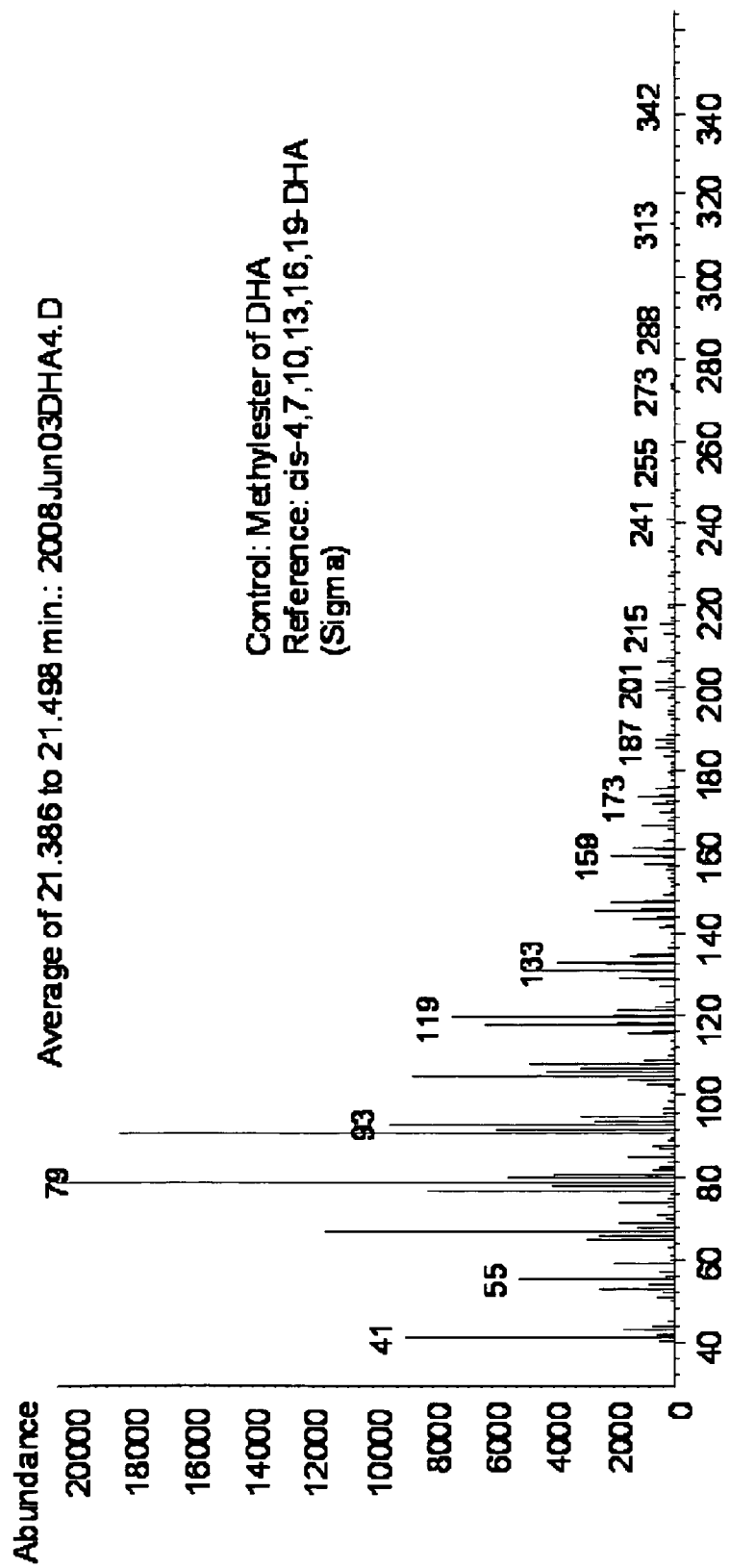

cont. of Figure 4:
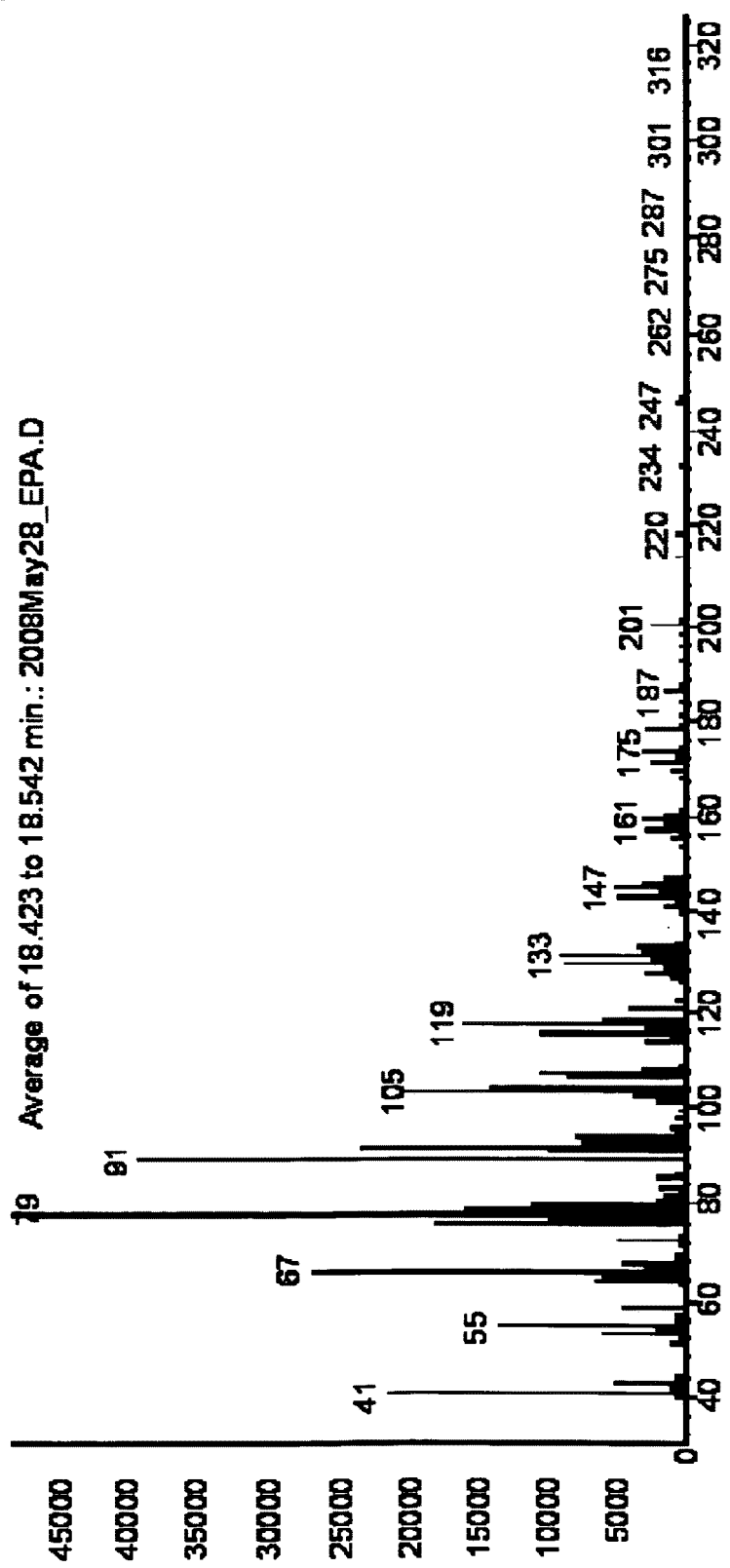

cont. of Figure 5:

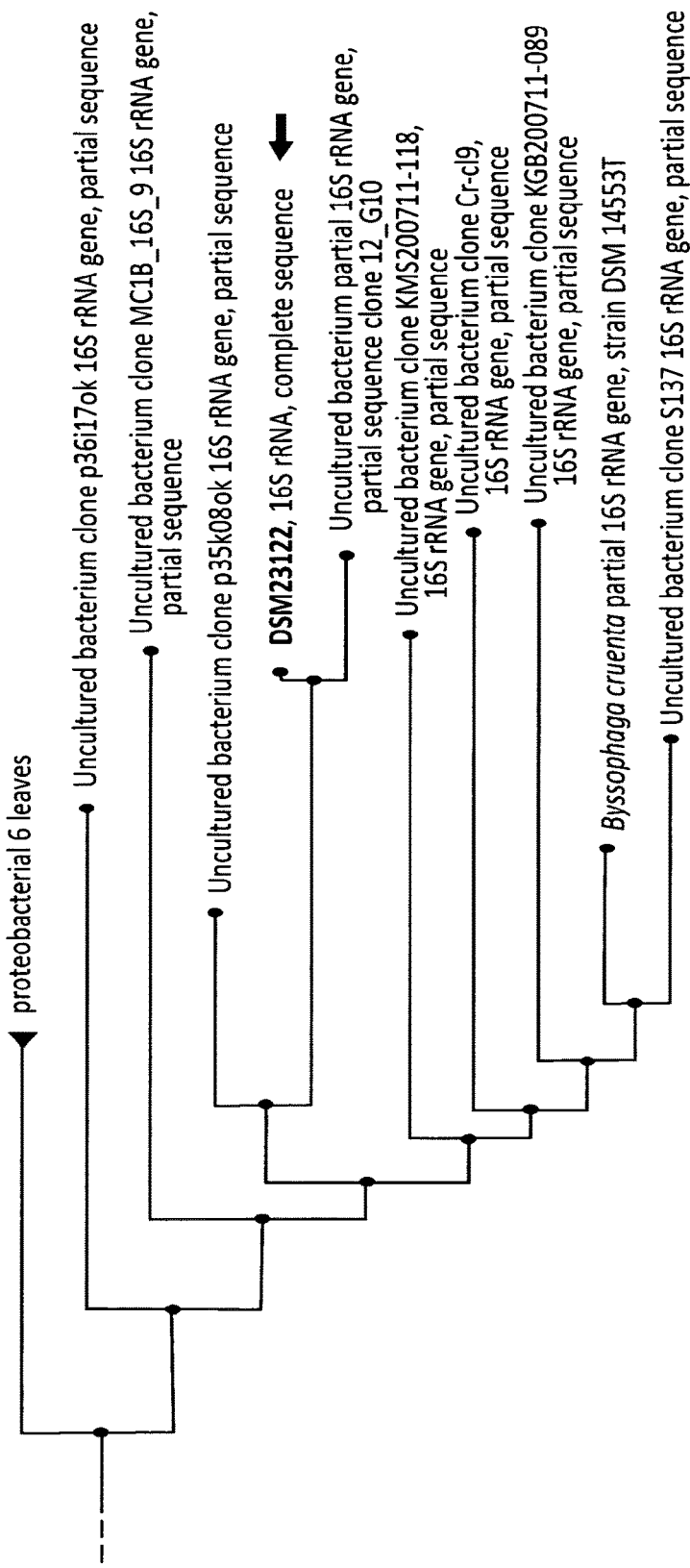
Cont. of Figure 6:

PRODUCTION OF OMEGA-3 FATTY ACIDS BY MYXOBACTERIA

The present invention provides a method for producing omega-3 polyunsaturated fatty acids (PUFAs) by culturing specific myxobacterial stains suitable for said method. In addition, it provides a method for identification of such omega-3 producing myxobacteria by using phylogenetic analyses based on 16S rDNA sequence data in combination with physico-chemical data based on gas chromatography coupled with mass spectroscopy to discover further producers of the omega-3 polyunsaturated fatty acids.

BACKGROUND OF THE INVENTION

Long-chain polyunsaturated fatty acids (PUFAs), including those of the omega-3 family [also known as ω-3 ("omega-3") fatty acids] are interesting fatty acids in nature. They are important constituents of phospholipids that play a role in decreasing membrane rigidity. Eicosapentaenoic acid (EPA) is a major constituent of the human brain's phospholipids and serves as precursor of prostaglandins and resolvins. Another important PUFA of the omega-3 family is docosahexaenoic acid (DHA). Improved cognitive and behavioural function in infant development seems correlated to high levels of this compound. For omega-3 PUFAs, and in particular for DHA and EPA, beneficial health effects have been e.g. the prevention of cancer, rheumatoid arthritis, cardiovascular diseases, the improvement of immune function, and eye and brain health [for recent overview see Teale M C (ed.) (2006) Omega-3 fatty acid research. Nova Science Publishers. New York, and references therein]. Because of these beneficial properties omega-3 PUFAs are being used extensively as nutritional lipids in health and dietary supplements and as functional ingredients in a wide range of foods. Omega-3 PUFAs presently comprise one of the biggest and strongest growing market segments in the food and beverage industry sector, with substantially increasing demand over the past years.

These days, fish oil is the most abundant and widely used natural source for omega-3 fatty acids, but named source suffers from over fishing, lack in high grade oil supply with sufficient content of DHA/EPA, and quality issues (smell, formulation challenges etc.). Alternative processes involving algae and oomycetes as producer organisms are established or under development [see overviews by Hinzpeter I et al. (2006) Grasas y Aceites 57:336-342 and Ward O P, Singh A (2005). Process Biochemistry 40:3627-3652, respectively]. Since the supply of fish oil of high quality is increasingly limited, it was attempted to find alternative, sustainable biological sources. Various groups of marine algae have been explored for over 20 years and some products based on algal biomass have meanwhile entered the market. Some oomycetes belonging to the group of stramenopiles (a group of algae-like eukaryontic organisms previously known as "Chromophyta") were also occasionally reported to produce the above mentioned compounds (e.g. of the genera *Achyla* and *Pythium*; [Aki T et al. (1998) J Ferm Bioengin 86:504-507; Cheng M H et al. (1999) Bioresour Technol 67:101-110; Athalye S K et al. (2009) J Agric Food Chem 57:2739-2744]). In other stramenopiles (e.g. the genera *Schizochytrium* and *Thraustochytrium*; as described in U.S. Pat. No. 7,022,512 and WO2007/068997) and in species of the dinoflagellate *Amphidinium* (US 2006/0099694), DHA may represent up to 48% of the fatty acid content of the cells, which are the highest contents so far known in the Eukaryota. However, the cultivation of these organisms in industrial scale still poses a challenge even after several years of development.

Other alternative biological sources for omega-3 PUFAs hitherto found are prokayotic eubacteria [Nichols D et al. (1999), Curr Opin Biotechnol 10:240-246; Metz J G et al. (2001), Science 293:290-293; Gentile G et al. (2003) J Appl Microbiol 95:1124-1133]. However, the commercial exploitation of these organisms for PUFA production on an industrial scale is hampered by the slow growth characteristics of these psychrophilic microorganisms, as well as their inherently low yields and productivity. In myxobacteria, an unidentified PUFA with 20 carbon atoms and four double bonds was found first in marine genera of *Plesiocystis* and *Enhygromyxa* [Iizuka T et al. (2003) Int J Syst Evol Microbiol 53:189-195; Iizuka T. et al. (2003), Syst Appl Microbiol 26:189-196]. Recently, ARA (an omega-6 PUFA) was encountered in *Phaselicystis flava*, a representative of a novel myxobacterial family [Garcia R O et al. (2009), Int J Syst Evol Microbiol 50(PT12):1524-1530].

The occurrence of omega-3 PUFAs like DHA and EPA is not reported at all for Myxobacteria and so far described processes are insufficient with regard to yields, amount of PUFAs and especially concerning the production of the important omega-3 PUFAs.

Myxobacterial Taxonomy and Phylogeny

The myxobacteria are believed to have evolved as a monophyletic group of organisms in the order Myxococcales, a delta subgroup in proteobacteria. At present, 3 suborders (Cystobacterineae, Nannocystineae, and Sorangiineae) are recognized in myxobacteria [Reichenbach H (2005) Order VIII. Myxococcales Tchan, Pochon and Prevot 1948, 398AL. In Brenner D J, et al. (eds.) Bergey's Manual of Systematic Bacteriology, 2nd edn, vol. 2, part C, pp. 1059-1072, New York: Springer]. These suborders are divided into six families, namely Cystobacteraceae, Myxococcaceae, Nannocystaceae, Kofleriaceae, Polyangiaceae, and Phaselicystidaceae.

The family Myxococcaceae is composed of the genera *Myxococcus, Corallococcus* and *Pyxidicoccus*. In the related family Cystobacteraceae, five genera are known (*Cystobacter, Archangium, Hyalangium, Melittangium* and *Stigmatella*). Nannocystaceae of the suborder Nannocsytineae are comprised of the Nannocystis and two marine genera (*Enhygromyxa* and *Plesiocystis*). Its related family Kofleriaceae is composed of the terrestrial genus *Kofleria* and the marine genus *Heliangium*. The family Polyangiaceae encompasses the genera *Jahnella, Chondromyces, Polyangium, Byssovorax*, and *Sorangium*. So far, the latter two are the only known genera of cellulose degraders among the order; most of the other taxa are difficult to isolate and cultivate. The recently discovered genus *Phaselicystis* is the only genus in the recently erected family Phaselicystidaceae [Garcia R O et al. (2009) Int J Syst Evol Microbiol 59:1524-1530]. At present 20 genera are recognizable and validly described in myxobacteria to cover all the known soil and marine isolates.

General Importance of 16S rDNA in Bacterial Taxonomy and Phylogeny.

16S rDNA has been widely and commonly used in bacterial systematics to designate ancestral groupings of the taxa because this gene is highly conserved between species [Weisburg W G et al. (1991) J Bacteriol 173:697-703]. In myxobacteria, the 16S rDNA phylogeny along with morphological characteristics provides a strong evidence for genetic classification [Spröer C et al (1999), Int J Syst Bacteriol 49(PT 3):1255-1262]. Those myxobacterial strains assigned to the same genus by morphological classification were found to be tightly clustered in their 16S rDNA gene phylogeny. This method also provides patterns for ancestral relatedness among its member species which are reflected on the degree of phenotypic characteristics [Vellicer G J, Hillesland K (2008) In Myxobacteria: Multicellularity and Differentiation (Whitworth D E, ed.), pp. 17-40, Washington, D.C.:ASM Press].

Importance of Fatty Acid Profiles as Chemotaxonomic Markers in Bacteria

The phylogeny is in accordance with the morphological and physiological characteristics of myxobacteria. Most importantly, fatty acid profiles as inferred from GC-MS analyses of the cellular fatty acid content are generally used and deemed acceptable for taxonomic segregation of Myxobacteria, as well as many other groups of bacterial organisms, since they were found to be a constant feature, at least when standardised methodology is applied. First applications of this technique have been made in the early 1989s [Tornabenet G (1985) Methods in Microbiology 18, 209-234]. Therefore, such GC-MS (or GC-) based fatty acid profiles have been widely used in bacterial phylogeny and taxonomy. Nevertheless, a systematic approach combining both the search for particular economically important fatty acids in combination with other means of investigation to evaluate the taxonomic and phylogenetic positions of the respective fatty acid producers has so far never been carried out.

Importance of PCR-Based Methods to Explore Bacterial Species Diversity and Functional Biodiversity in Ecosystems It has been discussed for a long time (and meanwhile proven by methods of molecular biology directed at the in situ identification of eubacteria in environmental samples) that the overall diversity of extant bacterial species is much higher than the number of known and well-described, culturable species [Amann R I et al. (1995) Microbiol Rev 59:143-169; Torsvik V et al. (1990) Appl Environ Microbiol 56:782-787]. According to current estimates, as much as 90% of the extant bacteria still remain to be discovered. Using methods such as direct sequencing of 16S rDNA from soil and other environmental samples is increasingly revealing a great diversity of DNA sequences that cannot be correlated to any of the known, culturable bacterial species. However, their phylogenetic affinities may be revealed from a homology comparison of their 16S rDNA with those of reference strains. Metagenomic techniques, which are currently under development, may in future eventually facilitate the direct utilisation of the genes and enzymes of these "unculturable" organisms. At present it remains necessary in most cases to find suitable culture conditions for the hitherto unexplored bacterial organisms and explore them at the stage of their pure cultures. As prerequisite for the characterisation of all the unexplored bacteria, as well as for their biotechnological exploitation, especial isolation techniques need to be established. This is also true in particular with regard to the discovery of novel myxobacterial taxa, as well as for various other groups of eubacteria and other microbial groups with great potential on biotechnology.

Myxobacterial groups can be specifically searched for by PCR using specific 16S rDNA primers. A previous study on a soil niche revealed at least 30 additional unknown phylogenetic groups of myxobacteria that could be detected using this approach. They are not only different from each other, but also their 16S rDNA genes differed from those of the known myxobacterial 16S rDNA gene sequences existing in GenBank and other public domain databases. These results suggested the presence of a vast undiscovered diversity of soil myxobacteria that yet remain to be cultured and explored [Zhi-Hong W. et al. (2005) Env. Microbiol. 7(10): 1602-1610].

Microbial Fermentation, with Particular Emphasis on Myxobacteria

Myxobacterial strains are usually fermented in an aqueous nutrient medium under submerged aerobic conditions. Various examples for the feasibility of large scale fermentation of this group of organisms in pilot and industrial scale are widely known to science, e.g., concerning the discovery and development of the epothilones, which have recently been approved as anticancer drugs.

After the thorough evaluation of their growth and nutrient conditions, these organisms can normally be grown well in laboratory culture and their production be scaled up in a straightforward manner. Typically, microorganisms are fermented in a nutrient medium containing a carbon source and a proteinaceous material. Preferred carbon sources include glucose, brown sugar, sucrose, glycerol, starch, corn starch, lactose, dextrin, molasses, and the like. Preferred nitrogen sources include cottonseed flour, corn steep liquor, yeast, autolysed brewer's yeast with milk solids, soybean meal, cottonseed meal, corn meal, milk solids, pancreatic digest of casein, distillers' solids, animal peptone liquors, meat and bone scraps, and the like. Combinations of these carbon and nitrogen sources can be used advantageously. There is no need to add trace metals, e.g. zinc, magnesium, manganese, cobalt, iron and the like to the fermentation medium since tap water and unpurified ingredients are used as medium components.

Large scale fermentation for production cultures can be induced at any temperature conductive to satisfactory growth of the microorganisms between about 18° and 32° C. and preferably at about 28° C. Ordinarily, optimum production of compounds is obtained in about 2 to 8 days of fermentation, and preferably in about 4 to 5 days of fermentation.

Production can be carried out in shake flasks but also in solid media and stirred fermentors. When growth is carried out in shake flasks or large vessels and tanks, it is preferable to use the vegetative form, rather than the spore form of the microorganism for inoculation. This avoids a pronounced lag in the production of the PUFA compounds and the attendant inefficient utilisation of the equipment. Accordingly, it is desirable to produce a vegetative inoculum in an aqueous nutrient medium by inoculating this medium with an aliquot from a soil or a slant culture. When a young, active vegetative inoculum has thus been secured, it is transferred aseptically to other shake flasks or other suitable devices for fermentation of microorganisms. The medium in which the vegetative inoculum is produced can be the same as, or different from, that utilised for the production of compounds, as long as adequate growth of the microorganism is obtained.

In general, seeding of myxobacterial strains and fermentation and the production of compounds in submerged aerobic fermentation in stirred vessels is utilised. The production is independent of used containers, fermentors and starter proceedings. The compounds can also be obtained by shake-flask culture, or in other specially designed vessels such as airlift or Biowave fermentation tanks. For large volume fermentations it is preferable to use a vegetative inoculum. The vegetative inoculum is prepared by inoculating small volume of culture medium with the spore form or a lyophilised pellet of the organism. The vegetative inoculum is then transferred to a fermentation vessel where, after a suitable incubation time, compounds are produced in optimal yield.

As is customary in aerobic submerged culture process, sterile air is dispersed through the culture medium. For efficient growth of the organism, the volume of the air used is in the range of from about 0.25 to about 0.5 vvm. An optimum rate in a 10 l vessel is about 0.3 vvm with agitation provided by conventional impellers rotating at about 240 rpm. Adding of small amount (i.e. 1 ml/l) of an antifoaming agent such as silicone to fermentations media is necessary if foaming becomes a problem. For microaerophilic organisms it may be favorable to reduce the aeration further in order to support biomass production. The fermentation is usually carried out in batch mode, but to attain better growth and increased product yield, fed-batch fermentations can be carried out by supplying the required nutrient source to a growing culture once it has been depleted in the original culture medium.

The desired products will usually be present mostly in the biomass of the fermented myxobacterial strains, but in case of their overproduction, they may as well be located in the culture filtrate of the fermentation broth. The culture broth can be separated by filtering on a filter press. A variety of procedures can be employed to isolate and purify the PUFA compounds from the fermentation broth, for example, by chromatographic adsorption procedures followed by elution with a suitable solvent, column chromatography, partition chromatography, by supercritical fluid extraction, and combinations of the aforementioned methods.

SUMMARY OF THE INVENTION

In the course of the characterization and identification of hitherto unknown myxobacterial strains of the suborder Sorangiineae, all to be classified in a hitherto unknown, newly discovered genus for which the name *Aetherobacter* is proposed here, were surprisingly found to produce significant amounts of polyunsaturated fatty acids (PUFAs), in particular omega-3 polyunsaturated fatty acids such as EPA and DHA. Three overproducers of EPA and DHA were found, which were designated as *Aetherobacter fasciculatus* sp. nov. ined, represented by strain DSM 21835, *Aetherobacter rufus* sp. nov. ined., represented by strain DSM 23122 and *Aetherobacter* sp. DSM 23098, This invention also relates to the surprising novel discovery that certain other strains of species belonging to class myxobacteria (in particular, strains of the genera *Enhygromyxa* and *Sorangium*) were also found to produce of DHA and EPA to a lower extent. At the same time, a screening of phylogenetically related bacteria based in published DNA sequences in public databases revealed several "uncultured" bacteria as closest relatives of the newly obtained omega-3 PUFA overproducing strains, which are presumably also myxobacteria.

This phylogenetic group of bacteria is believed to be widely unexplored for its biological diversity, hence it appears highly probable that additional new and hitherto unstudied taxa and strains that produce DHA and/or EPA in substantial quantities might be found in the near future. This can be facilitated by using a similar screening approach to that performed in the course of the discovery of the PUFA-producing strains that are subject of this application. This does not only concern additional new strains of the novel, yet inedited genus *Aetherobacter*, but even novel strains of other orders and families of myxobacteria.

DETAILED DESCRIPTION OF THE INVENTION

Figure 1:
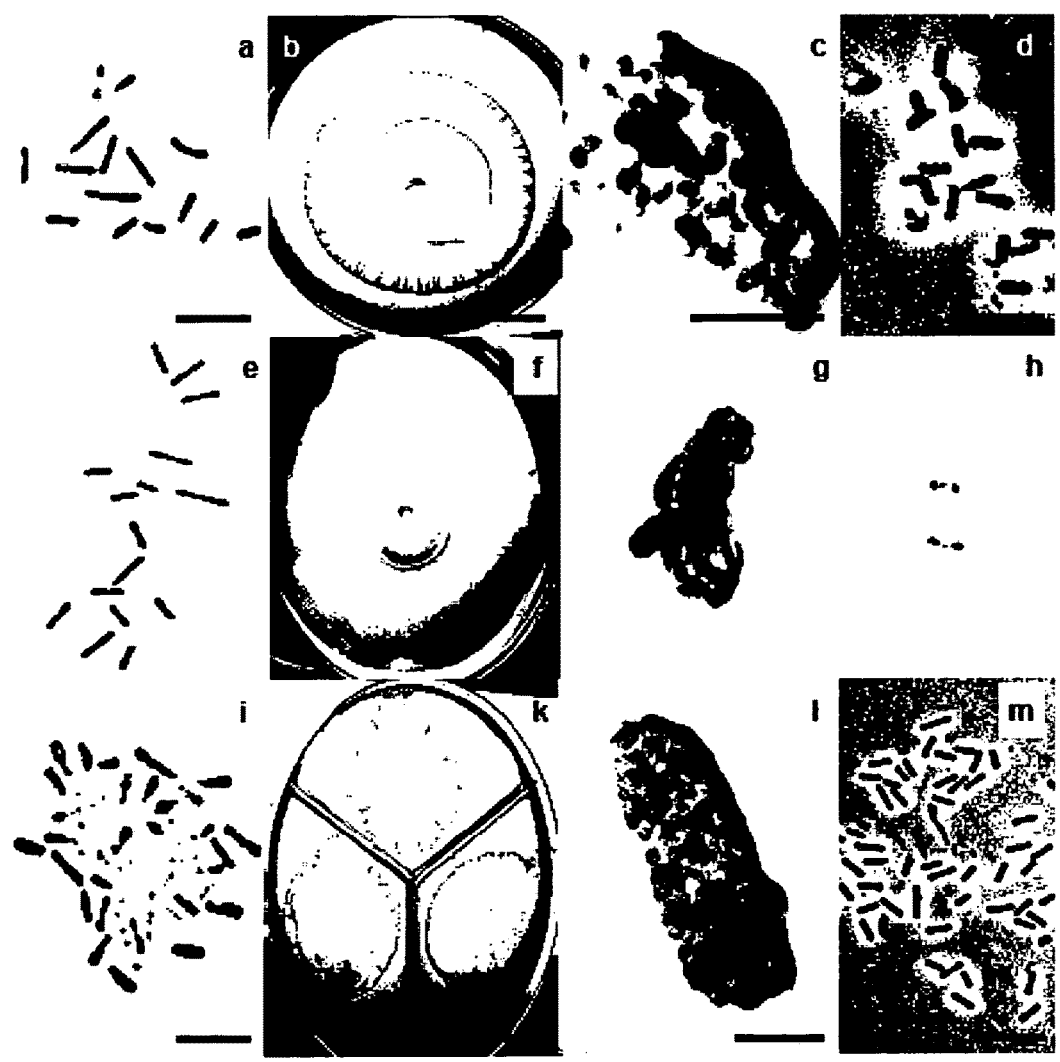
FIG. 1: Growth stages of '*Aetherobacter fasciculatus*' DSM 21835 (a-d), '*Aetherobacter rufus*' DSM 23122 (e-h), and *Aetherobacter* sp.' DSM 23098 (i-l). Phase-dark vegetative cells (a, e, i). Bar, 10 μm. Swarming colony on VY/2 agar showing typical clearing of the yeast cells (b, f, j). Bar, 15 mm. Dissecting photomicrographs of fruiting bodies on VY/2 agar (c, g, k). Bar, 300 μm. Slightly refractive myxospores from crushed sporangioles (d, h, l). Bar, 10 μm.

The myxobacterial strains of the invention are proposed to be classified in a novel genus *Atherobacter* and its novel species *A. fasciculatus, A. rufus* and as a yet unnamed *Aetherobacter* species. All of them were isolated from soil and plant debris samples originally collected in Indonesia in 1962. The samples had been preserved at the Zentrum für Biodokumentation, Landsweiler-Reden, Germany. For the isolation of myxobacteria the soil/plant debris samples were processed using live *Escherichia coli* as bait, following a previously described method [Reichenbach H & Dworkin M (1992) The Myxobacteria, In The Prokaryotes, 2nd edn, pp. 3416-3487 (Balows A et al., eds) New York: Springer].

*Aetherobacter fasciculatus* DSM 21835 was isolated in November 2007 from a soil sample containing pieces of roots and other decaying plant materials. The strain *A. rufus* DSM 23122 was isolated in December 2007 and *Aetherobacter* sp. DSM 23098 was isolated in February 2009.

The above myxobacterial strains belong to the suborder Sorangiineae of the order Myxococcales and are representatives of the novel inedited genus *Aetherobacter* and novel inedited species (*A. fasciculatus, A. rufus, Aetherobacter* sp.) proposed herewith, being aerobic to facultatively aerobic and chemoheterotrophic, having 16S rDNA sequences as shown in SEQ ID NO: 1 (DSM 21835), SEQ ID NO: 2 (DSM 23122) and SEQ ID NO: 4 (DSM 23098) that are about 96% identical with that of strain *Byssovorax* (syn. *Byssophaga*) *cruenta* DSM 14553$^T$ (GenBank Acc. No AJ833647, SEQ ID NO: 3) and/or having omega-3 PUFA contents of at least 10%, preferably at least 15% by weight of total cellular fatty acid content. In the following a description of the proposed taxa is provided.

The scientific names of the strains of the invention are still unpublished. There are no other strains known from the art of the genus *Aetherobacter*. This genus is described for the first time in this invention. Its phylogenetic relations are outlined as follows. The characteristics are outlined below, and, in more detail, in the examples.

Myxococcales include the following exemplified suborders which in turn include the following exemplified families, exemplified genera and exemplified species.

| suborder | family | genus | species (examples) |
| --- | --- | --- | --- |
| Cystobacerineae | Cystobacteraceae | Archangium | |
| | | Cystobacter | |
| | | Hyalangium | |
| | | Melittangium | |
| | | Stigmatella | |
| | Myxococcaceae | Anaeromyxobacter | |
| | | Corallococcus | |
| | | Myxococcus | |
| | | Pyxidiococcus | |
| Nannocystineae | Haliangiaceae (Kofleriaceaea) | Haliangium | |
| | Nannocystaceae | Nannocystis | |
| | | Plesiocystis | |
| | | Enhygromyxa | *Enhygromyxa salina* |
| Sorangiinae | Phaselicystidaceae | Phaselicystis | |
| | Polyangiaceae | Polyangium | |
| | | Jahnella | |
| | | Chondromyces | |
| | | Byssovorax | *Byssovorax cruenta* |
| | | Aetherobacter | *Aetherobacter fasciculatus* (DSM 21835) |
| | | | *Aetherobacter rufus* (DSM 23122) |
| | | | *Aetherobacter* sp. (DSM 23098) |
| | | Sorangium | *Sorangium cellulosum* |

The phylogenetic relationships as inferred from a comparison of 16S rDNA sequence data of representative genera and species of which viable cultures are extant, are presented in FIG. 10.

The three novel strains are morphologically rather similar. *Aetherobacter fasciculatus* DSM 21835 shares nearly the same growth stages appearance with *Aetherobacter* sp. DSM 23098, with regard to the vegetative cells as well as the fruiting bodies. *Aetherobacter rufus* DSM 23122 differs in having red fruiting bodies and smaller sporangioles. In addition, DSM 23122 produced a whitish swarm that differs in the yellowish orange color of the remaining two strains of *Aetherobacter*.

Physiological tests also revealed differences among the novel strains and species. Obviously the three novel strains prefer different sugars and nitrogen sources for growth. The antibiotic resistance seems to distinguish isolates, e.g., DSM 21835 and DSM 23098 appear resistant to Hygromycin B, whereas DSM 23122 is sensitive to this compound. Resistance to ampicillin and neomycin differentiates *A. fasciculatus* DSM 23098 and *A. rufus* DSM 23122 from strain DSM 23098. It also appears that DSM 21835 and DSM 23098 exhibit a wider range of antibiotic resistance in comparison to DSM 23122.

The 16S rDNA sequences derived from the three novel strains clustered together in the phylogenetic tree, supported by 100% bootstrap value. *Aetherobacter fasciculatus* DSM 21835 appears not only morphologically similar to *A.* sp. DSM 23098, but the 16S rDNA sequences also showed a high degree of homology (99.4% identity). *A. rufus* DSM 23122 was found 98.9% identical with DSM 21835 and 99.2% with DSM 23098. This relationship is notable in the phylogenetic tree where sequences of DSM 21835 clustered together with DSM 23098, rather than with DSM 23122 (FIG. 10).

Description of New Genus and Species

1. *Aetherobacter* R. O. Garcia & R. Müller, Gen. Nov. Ined.

Entymology: *Aetherobacter* [Ae.the.ro.bac'ter. Gr. masc. n. Aether Greek God of Light (refers to clear and transparent swarming); Gr. fem. n. bacter from Gr. neut. n. bakterium small rod, stick; M.L. masc. n. *Aetherobacter* clear swarming rod]

Vegetative cells moderately long and slender cylindrical rods with blunt ends; movement by gliding on surface and under the agar. Swarm, film-like to transparent-clear colony. Congo-red-negative, edges characterized by coherent migrating cells, penetrating mostly under the solid medium; agar slightly depressed. Myxospores refractive slender rods with blunted ends, shorter than vegetative cells, enclosed in sporangial wall. Fruiting bodies as tiny ovoid sporangioles, usually compact or clustered. Yeasts are completely degraded. Strongly bacteriolytic. With omega-3 polyunsaturated fatty acids as major components of cellular FA. Percent G+C, 68.0-70%.

The novel genus *Atherobacter* is clearly different from the most similar accepted genus of *Myxobacteria, Byssovorax* in many ways. Morphologically, *Byssovorax* shows an intense red pseudoplasmodia-like swarm and fruiting bodies on agar medium. This independent flocks of migrating cells is regarded as very characteristic of that genus. The sporangioles are large (60-180 µm wide) and also show intense red colors. In contrast, the species of the novel genus *Aetherobacter* as represented by the strains described in detail further below produce a swarming pattern that deeply penetrates the agar. The swarm created by the burrowing cells of *Aetherobacter* spp. rather shows a radial (circular) appearance. In addition, the swarming cells exhibit white to light orange colours. The center of the colonies in all these novel strains are usually clear in yeast agar (VY/2). The single sporangiole is small (<20 µm) and arranged in tightly packed clusters or bundles that are often located within the agar.

Another significant difference between *Aetherobacter* spp. and *Byssovorax* is the inability of the members of the new genus to degrade cellulose. Both genera also differ significantly in their fatty acid profiles. *Byssovorax* contains a higher amount of iso-15:0 and straight chain fatty acids and is devoid of DHA and EPA.

The genetically characteristic of a 96% similarity of the 16S rDNA was also used for the recently erected myxobacterial genera *Enhygromyxa* [Iizuka T. et al. (2003) Syst Appl Microbiol 26:189-196] and *Byssovorax* [Reichenbach et al., 2006. Int J Syst Evol Microbiol. 56(PT 10): 2357-2363].

Based on the aforementioned data, the novel *Aetherobacter* strains appear significantly different from the known genus *Byssovorax*, i.e. the myxobacterial genus that appears most closely related as inferred from a homology comparison of their 16S rDNA. Taken together these differences in morphology, chemo-physiology, topology of the 16S rDNA gene, and phylogenetic analysis suggest in unison that the erection of a new genus is justified.

2. *Aetherobacter fasciculatus* R. O. Garcia & R. Müller, Sp. Nov. Ined.

Entymology: *fasciculatus* [fasc.i.cu'la. L. masc. n. *fasciculum* little bundles or packets (refers to the arrangement of sporangioles)].

With all characteristics of the genus. Vegetative cells fat rods, 1.2-1.3×2.9-5.7 µm in size, and phase dark. Swarms are orange tint which show complete clearing of the yeast cell bait, with shallow depression on surface of the agar, often deeply penetrating the medium to form coherent curtain-like structures. Fruiting bodies are yellow-orange in color, often found under the agar, as sod (30×50 µm) composed 5-20 tiny sporangioles (10.4×11.4 µm) tightly arranged as bunch. Myxospores refractive, stout rods, with rounded ends similar but shorter (1.0-1.2×3.2-4.0 µm) than vegetative cells; enclosed in a sporangial wall. Nutritional type, bacteriolytic, yeast degrader. Cellulose and chitin not degraded. Good growth in saccharose, fructose, D-mannose and L-arabinose. Resistant to broad spectra of antibiotics: gentamycin, apramycin, tobramycin, streptomycin, ampicillin, neomycin and hygromycin B. Sensitive to kanamycin, spectinomycin, tetracycline, oxytetracycline, carbenicillin, and rifampicin. Major cellular fatty acid components are $C_{22:6}$ (docosahexaenoic acid, DHA) iso-$C_{15:0}$, $C_{20:5}$. (eicosapentaenoic acid, EPA). Mol percent G+C is 68.9.

Type Strain:

*Aetherobacter fasciculatus* was deposited according to the Budapest Treaty at the DMSZ, Deutsche Sammlung von Mikroorganismen and Zellkulturen GmbH, Inhoffenstr. 7 B, 38124 Braunschweig, Germany on Aug. 27, 2008 with the deposition number DSM 21835.

*A. fasciculatus* DSM 21835 has a 16S rDNA sequence that is 96% identical to that of *Byssovorax* (syn: *Byssophaga*) *cruenta* DSM 14553$^T$. It shows an omega-3 PUFA content of at least 10%, preferably at least 15% by weight of the total cellular fatty acid content.

*A. fasciculatus* DSM 21835 was identified as member of class Myxobacteria, order Myxococcales by showing characteristic swarming of Gram-negative, slender rod-shaped vegetative cells, fruiting body formation, and bacteriolytic activity. The strain is aerobic to facultative aerobic, chemoheterotrophic, and also exhibits resistance to various antibiotics. Major fatty acids are $C_{22:6}$ (docosahexaenoic acid), iso-$C_{15:0}$, anti-iso $C_{17:0}$ and $C_{20:5}$ (eicosapentaenoic acid). The G+C content of the genomic DNA is 68.9 mol %. The 16S rDNA sequence shows 96% identity to the cellulose-degrading *Byssovorax cruenta* and 95% to *Sorangium cellulosum*. This clearly shows that the strain belongs to the suborder Sorangiineae of the order Myxococcales. In addition, uniqueness in morphological growth stages and novel fatty acid profile, clearly implies that DSM 21835 belongs to a new taxon which is proposedly classified as belonging to the novel genus *Aetherobacter* and in the novel species *A. fasciculatus*

3. *Aetherobacter rufus* R. O. Garcia & R. Müller, Sp. Nov. Ined.

Etymology: *rufus* (ru.fus. L. masc. adj. *rufus* red).

With all the characteristics of the genus. Vegetative cells fat rods, 1.0-1.2×3.0-6.0 µm in size, longest 15 µm, phase dark. In yeast agar, the swarm moves coherently in the medium to form a ring or circular structure, with white edge color. Colonies on (VY/2 agar) appear clear and transparent as a result of complete yeast degradation. On the surface of the agar, they are often produced as thin sheet or film with mounds of cell aggregates toward the colony edge, exhibiting shallow agar depressions. Fruiting bodies showing red to vermilion color, appearing as a simple mound (120×140 µm), or as very long rolls (340×400 µm-1900×2900 µm), visible to the naked eye, initially developing from white humps of cellular aggregation. Composed of tiny sporangioles (6-12 µm), compacted in a sorus (14×15 µm-16×26 µm). Myxospores refractive, stout and short rods (1.0-2.0 µm), with rounded ends like the vegetative cells; enclosed in the sporangial wall. Nutritional type bacteriolytic. Cellulose and chitin not degraded. Equally good growth in all sugars tested: L-arabinose, fructose, galactose, D-glucose, D-mannose, molasses, sorbitol, xylose, cellobiose, lactose, maltose, saccharose, and soluble starch. Resistant to ampicillin, neomycin and gentamycin. Sensitive to apramycin, tobramycin, kanamycin, spectinomycin, hygromycin B ampicillin, tetracycline, oxytetracycline, streptomycin, carbenicillin, and rifampicin, major cellular fatty acid components are iso-$C_{15:0}$, $C_{22:6}$ (DHA), $C_{15:0}$, $C_{16:0}$. Also produces $C_{20:5}$. (EPA). Mol percent G+C is 68.0.

Type Strain:

*Aetherobacter rufus* was deposited at the Deutsche Sammlung von Mikroorganismen and Zellkulturen GmbH (DSMZ), Braunschweig, Germany, at Jul. 10, 2009 under the deposition number DSM 23122.

*A. rufus* strain DSM 23122 was also found to produce EPA and DHA. Morphologically this strain shares many similarities with *A. fasciculatus* strain DSM 21835. However, the two species differ in several physiological characteristics such as antibiotic sensitivities, carbon requirement, pH tolerance and in the 16S rDNA sequence. In the analysis of omega-3 fatty acids, *A. rufus* DSM 23122 also produces both DHA and EPA.

4. *Aetherobacter* sp. DSM 23098

*Aetherobacter* sp. DSM 23098 was also found to be related to the above mentioned strains and to contain omega 3-PUFAs in substantial quantities in its cellular biomass. This strain was therefore also deposited according to the Budapest Treaty at the DMSZ, Nov. 12, 2009 with the deposition number DSM 23098.

The general expressions, within the present disclosure, preferably have the following or precedingly mentioned meanings, where in each embodiment on, more than one or all more general expressions may, independently of each other, be replaced with the more specific definitions, thus forming preferred embodiments of the invention, respectively.

Preferably, the following abbreviations are used for the purpose of the invention:

| Abbreviation | Explanation |
|---|---|
| 16S rDNA | gene encoding for a part of the small ribosomal subunit in prokaryotes |
| ARA | Arachidonic acid |
| BD | Becton Dickenson, Le Pont de Claix, France |
| DHA | Docosahexenoic acid [(4Z,7Z,10Z,13Z,16Z,19Z)-docosa-4,7,10,13,16,19-hexaenoic acid] |
| DSM | Designation number of strains deposited in Deutsche Sammlung von Mikroorganismen and Zellkulturen (DSMZ) |
| EDTA | Ethylenediamine tetraacetic acid |
| EPA | Eicosapentenoic acid [(5Z,8Z,11Z,14Z,17Z)-eicosa-5,8,11,14,17-pentenoic acid] |
| FA | Fatty acid |
| FAME | Fatty acid methyl ester |
| GC | Gas chromatography |
| GC-MS | Gas chromatography coupled with mass spectrometry |
| HEPES | 2-(4-(2-Hydroxyethyl)-1-piperazinyl)-ethansulfonic acid |
| MS | Mass spectrometry |
| MSTFA | N-Methyl-N-(trimethylsilyl)trifluoroacetamide |
| Omega-3 fatty acids | (also n-3 fatty acids) Family of unsaturated fatty acids that have in common a carbon-carbon double bond in the n-3 position (the third bond counted from the terminal methyl group of the fatty acid) |
| Omega-6 fatty acids | (also n-6 fatty acids) Family of unsaturated fatty acids that have in common a carbon-carbon double bond in the n-6 position (the sixth bond counted from the terminal methyl group of the fatty acid) |
| PCR | Polymerase Chain Reaction |
| PUFA | Polyunsaturated fatty acid |
| vvm | Volume of air per volume of culture medium per minute |

Myxobacteria are preferably scientifically classified in the kingdom: bacteria, phylum: Proteobacteria, class: Delta Proteobacteria, order: Myxococcales.

For the purpose of the invention the terms "myxobycteria" and "myxobacterial strain" preferably refer to any species or other members of microorganisms belonging to the order of Myxococcales.

The used term "members" preferably is used for any myxobacterial strain of the invention which is defined as to be a homolog neighbour of *Aetherobacter*.

For the purpose of the invention all used taxonomic relations are in accordances to Brenner D J, et al. (eds.) Bergey's Manual of Systematic Bacteriology, 2nd edn, New York: Springer, especially the methods of the invention are referring to this standard.

For the purpose of the invention genetic affinity is described with the term of "homology". This is based on the use of 16S rDNA sequences for a binary comparison of a FASTA sequence (identified by their accession number as outlined in table 1) against the respective 16S rDNA of a specified strain of the present invention using the BLASTn 2.2.22 algorithm from the url http://blast.ncbi.nlm.nih.gov/Blast.cgi which is further described in Zhang Z et al. (2000) J Comput Biol 7:203-214.

An "omega-3 polyunsaturated fatty acid (PUFA)" according to the present invention includes eicosa-cis-5,8,11,14, 17-pentaenoic acid (20:5 EPA) and docosa-cis-4,7,10,13,16, 19-hexaenoic acid (22:6 DHA). The method of the first aspect of the invention is particularly useful for the production of EPA and DHA and mixtures of said fatty acids.

A preferred embodiment of the invention relates to the production of omega-3 unsaturated fatty acids which comprises culturing a myxobacterial strain capable of producing one or more omega-3 polyunsaturated fatty acids.

Preferably, a myxobacterial strain "capable" of producing omega-3 PUFAs is regarded to contain of at least 0.5% of omega-3 PUFAs determined as described in example 5, more preferably to contain at least 1%, still more preferably to contain at least 2%, yet more preferably to contain at least 5%, most preferably to contain at least 10% and in particular to contain at least 15% by weight of total cellular fatty acid content.

A preferred embodiment of the invention relates to a method, wherein the myxobacterial strain belongs to the suborder Sorangiineae of the order Myxococcales.

In a preferred embodiment the myxobacterial strain has a 16S rDNA sequence that is at least 84%, more preferably at least 85% or 86%, still more preferably at least 87%, 88%, 89% or 90%, yet more preferably at least 91%, 92% or 93%, most preferably at least 94%, 95%, 96% identical with the *Byssovorax* (*Byssophaga*) *cruenta* DSM 14553$^T$.

A preferred embodiment of the invention relates to a method, wherein the myxobacterial strain belongs to the suborder Polyangiaceae of the order Myxococcales.

In a preferred embodiment the myxobacterial strain has a 16S rDNA sequence that is at least 85% or 86%, more preferably at least 87%, 88%, 89% or 90%, still more preferably at least 91%, 92% or 93%, most preferably at least 94%, 95%, 96% identical with *Byssovorax* (*Byssophaga*) *cruenta* strain DSM 14553$^T$.

A preferred embodiment of the invention is related to a method, wherein the myxobacterial strain has an omega-3 polyunsaturated fatty acid content of at least 10%, preferably at least 15% by weight of total cellular fatty acid content.

In a further preferred embodiment the omega-3 unsaturated fatty acids are selected from eicosapentaenoic acid (EPA), docosahexaenoic acid (DHA) and mixtures thereof.

In a preferred embodiment of further methods of the invention said culturing includes a seed culture incubation of said myxobacterial strain and a subsequent main culture for omega-3 PUFA production. It is preferred that the seed culture is performed on a VY/2 (yeast medium) agar medium, most preferably in an MD1G agar. Moreover it is preferred that the culture is performed at a temperature of 25 to 32° C., preferably at about 30° C.

In another preferred embodiment of further methods of the invention the culturing for omega-3 PUFA production is performed in a liquid medium. In particular it is preferred that the culturing is performed in MD1G broth. Again, the culture is preferably performed at a temperature of 25 to 32° C., preferably at about 30° C. Another preferred mode of cultivation is performed in the same medium with pH adjusted to 7.0, under high volume medium, so as to reduce air.

In another preferred embodiment of the methods of the invention the method further comprises (i) isolating said one or more omega-3 PUFAs from the culture; and/or (ii) purifying said one or more omega-3 PUFAs; and/or (iii) isolating an individual omega-3 PUFAs.

In a further preferred embodiment the myxobacterial strain belongs to the suborder Sorangiineae of the order Myxococcales and is a representative of a novel genus (*Aetherobacter*) and novel species (*fasciculatus*) proposed herewith, being aerobic to facultative aerobic and chemo heterotrophic, having a 16S rDNA sequence that is about 96% identical with the *Byssovorax* (*Byssophaga*) *cruenta* DSM 14553[1] as shown in SEQ ID NO:3 and/or having an omega-3 polyunsaturated fatty acid content of at least 10%, preferably at least 15% by weight of total cellular fatty acid content.

In a preferred embodiment the myxobacterial strain has a 16S rDNA sequence that is at least 94%, more preferably at least 94.5% or 95%, still more preferably at least 95.5%, 96%, 96.5% or 97%, yet more preferably at least 97.5%, 98% or 98.5%, most preferably at least 99.0%, 99.2%, 99.4%, 99.6% or 99.8% identical with the 16S rDNA sequence shown in SEQ ID NO:1. In a particularly preferred embodiment the myxobacterial strain is *Aetherobacter fasciculatus* (DSM 21835) and is characterised by the 16S rDNA sequence shown in SEQ ID NO:1.

In a preferred embodiment the myxobacterial strain has a 16S rDNA sequence that is at least 94%, more preferably at least 94.5% or 95%, still more preferably at least 95.5%, 96%, 96.5% or 97%, yet more preferably at least 97.5%, 98% or 98.5%, most preferably at least 99.0%, 99.2%, 99.4%, 99.6% or 99.8% identical with the 16S rDNA sequence shown in SEQ ID NO:2. In a particularly preferred embodiment the myxobacterial strain is *Aetherobacter rufus* (DSM 23122) and is characterised by the 16S rDNA sequence shown in SEQ ID NO:2.

In a preferred embodiment the myxobacterial strain has a 16S rDNA sequence that is at least 94%, more preferably at least 94.5% or 95%, still more preferably at least 95.5%, 96%, 96.5% or 97%, yet more preferably at least 97.5%, 98% or 98.5%, most preferably at least 99.0%, 99.2%, 99.4%, 99.6% or 99.8% identical with the 16S rDNA sequence shown in SEQ ID NO:4. In a particularly preferred embodiment the myxobacterial strain is *Aetherobacter* sp. (DSM 23098) and is characterised by the 16S rDNA sequence shown in SEQ ID NO:4.

The invention is further illustrated by the following examples which are not to be construed as limiting its scope. The skilled person recognizes that the procedures used in the examples may be adapted in order to identify further individual myxobacterial strains capable of producing omega-3 PUFAs. For example, other known chromatographic methods and other known mass spectrometric methods may be employed differing from the exemplified methods that are described hereinafter.

General Experimental Procedures
Materials and Methods
List of Media Used in the Cultivation of Myxobacteria
CY-SWS

| | |
|---|---|
| Bacto Casitone (BD, Le Pont de Claix, France) | 1 g |
| Bacto Yeast extract (BD, Le Pont de Claix, France) | 0.3 g |
| Sea water salt (SWS) solution (see below) | ad 1 l |

Sea Water Salts Solution (SWS)

| | |
|---|---|
| Ferric citrate | 0.01 g |
| $MgSO_4 \times 7H_2O$ (Merck, Darmstadt) | 8 g |
| $CaCl_2 \times 2H_2O$ (Sigma-Aldrich, Seelze, Germany) | 1 g |
| KCl | 0.5 g |
| $NaHCO_3$ | 0.16 g |
| $H_3BO_3$ | 0.02 g |
| KBr | 0.08 g |
| $SrCl_2 \times 6H_2O$ | 0.03 g |
| Trace elements solution SL-4 (see below) | 1 ml |
| Distilled water | ad 1 l |

Trace Element Solution SL-4

| | |
|---|---|
| EDTA | 0.5 g |
| $FeSO_4 \times 7H_2O$ | 0.2 g |
| Trace element solution SL-6 (see below) | 100 ml |
| Distilled water | 900 ml |

Trace Element Solution SL-6

| | |
|---|---|
| $ZnSO_4 \times 7H_2O$ | 0.1 g |
| $MnCl_2 \times 4H_2O$ | 0.03 g |
| $H_3BO_3$ | 0.30 g |
| $CuCl_2 \times 2H_2O$ | 0.01 g |
| $NiCl_2 \times 6H_2O$ | 0.02 g |
| $Na_2MoO_4 \times 2H_2O$ | 0.03 g |
| Distilled water | ad 1 l |

HS-Medium

| | |
|---|---|
| $MgSO_4 \times 7H_2O$ (Merck, Darmstadt, Germany) | 0.1% (w/v) |
| $KNO_3$ (Sigma Aldrich, Seelze, Germany) | 0.1% (w/v) |
| Bacto Peptone (BD, Le Pont de Claix, France) | 0.15% (w/v) |
| TRIZMA Base (Sigma Aldrich, Seelze, Germany) | 0.2% (w/v) |
| NaFe-EDTA (Merck, Darmstadt, Germany) | 8 mg/l |
| Distilled water | ad 1 l |

Adjust pH to 7.2

Supplement after Autoclaving with the Following:

| | |
|---|---|
| $K_2HPO_4$ (Merck, Darmstadt, Germany) | 0.00625% (w/v) |
| Glucose (Merck, Darmstadt, Germany) | 0.4% (w/v) |
| $CaCl_2 \times 2H_2O$ (Merck, Darmstadt, Germany) | 0.0075% (w/v) |
| Distilled water | ad 1 l |

Soluble Medium M

| | |
|---|---|
| Bacto Phytone (BD, Le Pont de Claix, France) | 10 g |
| Maltose monohydrate (Merck, Darmstadt) | 10 g |
| $CaCl_2 \times 2H_2O$ (Sigma-Aldrich, Seelze, Germany) | 1 g |
| $MgSO_4 \times 7H_2O$ (Merck, Darmstadt) | 1 g |
| Ethylenediamine tetra acetic acid, iron (III)-sodium salt (Fluka, Buchs, Switzerland) | 8 mg |

-continued

| | |
|---|---|
| HEPES (Serva, Heidelberg) | 12 g/k |
| Distilled water | ad 1 l |

MD1 Liquid Medium

| | |
|---|---|
| Bacto Casitone (BD, Le Pont de Claix, France) | 0.3% (w/v) |
| $CaCl_2 \times 2H_2O$ (Sigma-Aldrich, Seelze, Germany) | 0.05% (w/v) |
| $MgSO_4 \times 7H_2O$ (Merck, Darmstadt) | 0.2% (w/v) |

Adjust pH to 7.0 with KOH

MD1G Liquid Medium

| | |
|---|---|
| Bacto Casitone (BD, Le Pont de Claix, France) | 0.3% (w/v) |
| $CaCl_2 \times 2H_2O$ (Sigma-Aldrich, Seelze, Germany) | 0.05% (w/v) |
| $MgSO_4 \times 7H_2O$ (Merck, Darmstadt) | 0.2% (w/v) |
| Glucose (Acros Organics, Geel, Belgium) | 0.35% (w/v) |

Adjust pH to 7.0 with KOH

VY/2 Liquid Medium

| | |
|---|---|
| Bakers' yeast ('Frischbackhefe', Nürnberg, Germany) | 0.5% (w/v) |
| $CaCl_2 \times 2H_2O$ (Sigma-Aldrich, Seelze, Germany) | 0.05% (w/v) |
| HEPES (Serva, Heidelberg) | 5 mM |
| Adjust pH to 7.0 with KOH | |

VY/2 Maltose

| | |
|---|---|
| Baker's yeast ('Frischbackhefe', Nürnberg, Germany) | 0.5% (w/v) |
| $CaCl_2 \times 2H_2O$ (Sigma-Aldrich, Seelze, Germany) | 0.05% (w/v) |
| Maltose monohydrate (Merck, Darmstadt) | 0.3% (w/v) |
| HEPES (Serva, Heidelberg) | 5 mM |

VY/2-SWS

| | |
|---|---|
| NaCl | 20 g |
| Bakers yeast ('Frischbackhefe', Nürnberg, Germany) (wet weight) | 2.5 g |
| Bacto agar (BD, Le Pont de Claix, France) | 15 g |
| Sea water salts solution (see below) | 1 l |

Adjust pH to 7.5 with 1M NaOH

LB Medium

| | |
|---|---|
| Bacto Tryptone (BD, Le Pont de Claix, France) | 10 g |
| Bacto Yeast extract (BD, Le Pont de Claix, France) | 5 g |
| NaCl (Difco) | 5 g |
| Distilled water | ad 1 l |

Adjust pH to 7.0 with KOH solution

VY/2 Agar Medium

| | |
|---|---|
| Bakers' yeast ('Frischbackhefe', Nürnberg, Germany) | 0.5% (w/v) |
| $CaCl_2 \times 2H_2O$ (Sigma-Aldrich, Seelze, Germany) | 0.05% (w/v) |
| HEPES (Serva, Heidelberg) | 5 mM |
| Agar (Difco) | 1.5% (w/v) |

Adjust pH to 7.0 with KOH

MD1G Agar Medium

| | |
|---|---|
| Bacto Casitone (Difco) | 0.3% (w/v) |
| $CaCl_2 \times 2H_2O$ (Sigma-Aldrich, Seelze, Germany) | 0.05% (w/v) |
| $MgSO_4 \times 7H_2O$ (Merck, Darmstadt) | 0.2% (w/v) |
| Glucose (Acros Organics, Geel, Belgium) | 0.35% (w/v) |
| Agar (Difco) | 1.5% (w/v) |

Adjust pH to 7.2 with KOH

Buffered Water Agar

| | |
|---|---|
| $CaCl_2 \times 2H_2O$ (Sigma-Aldrich, Seelze, Germany) | 0.1% (w/v) |
| Bacto Agar | 1.5% (w/v) |
| HEPES | 20 mM | pH adjusted to 7.0 with KOH solution

Mineral Salt Agar (ST21 Agar)
Solution A

| | |
|---|---|
| $K_2HPO_4$ | 0.1% (w/v) |
| Bacto Yeast extract | 0.002% (w/v) |
| Bacto Agar | 1% (w/v) |

Make up in about two-thirds of the water volume in distilled water.
Solution B

| | |
|---|---|
| $KNO_3$ | 0.1% (w/v) |
| $MgSO_4 \times 7H_2O$ | 0.1% (w/v) |
| $CaCl_2 \times 2H_2O$ | 0.1% (w/v) |
| $FeCl_3$ | 0.02% (w/v) |
| $MnSO_4 \times 7H_2O$ | 0.01% (w/v) |

Make up in the remaining water volume. Autoclave separately. Combine solutions A and B
CT 7Agar
Top Agar Layer

| | |
|---|---|
| $MgSO_4 \times 7H_2O$ | 0.1% (w/v) |
| $K_2HPO_4$ | 0.02% (w/v) |
| Chitin (Sigma) | 0.05% (v/v) |
| Bacto Agar | 1.5% (w/v) |

Adjust the pH to 7.5 with KOH, then poured as a thin layer on top of the base agar after autoclaving.
Base Agar Layer

| | |
|---|---|
| $CaCl_2 \times 2H_2O$ | 0.1% (w/v) |
| Bacto Agar | 1.5% (w/v) |
| HEPES | 5 mM |

Adjust the pH to 7.2 and autoclave.

Cel3 Agar

| | |
|---|---|
| Cellulose powder MN300 [Macherey and Nagel (Düren, Germany)] | 0.5% (w/v) |
| $KNO_3$ | 0.1% (w/v) |
| Bacto Agar | 1.0% (w/v) |

Adjust the pH to 7.2.

Separately autoclave the $KNO_3$, and add to the medium after the medium has cooled to about 50° C. Pour as a thin layer on top of mineral salt agar (ST21 agar).

Reference Strains

Several strains were used as references for the work performed in examples 5 and 6, and their reference DNA sequence data have been retrieved for comparison from public databases such as GenBank (a database provided by the National Center for Biotechnology Information; http://www.ncbi.nlm.nih.gov/) and/or respective databases generated by EMBL (European Molecular Biology Laboratory, http://www.embl.de/) They are all listed in table 1. Wherever possible, publications referring to these sequences were cited, and the sequence data are not depicted here.

TABLE 1

Reference DNA sequence data used for comparison with the novel myxobacterial strains of Aetherobacter spp. described in this patent application.

| Accession Number | Myxobacteria Species/Strains | Reference Literature |
|---|---|---|
| GU207872 | *Archangium gephyra* DSM 2261$^T$ | This study |
| AJ833647 | *Byssovorax cruenta* DSM 14553$^T$ | Reichenbach H. et al. (2006), Int J Syst Evol Microbiol. 56(PT 10): 2357-2363 |
| AJ233938 | *Chondromyces apiculatus* DSM14605$^T$ | Spröer C. et al. (1999), Int J Syst Bacteriol. 49(PT 3): 1255-1262 |
| GU207874 | *Chondromyces crocatus* DSM14714$^T$ | This study |
| AJ233939 | *Chondromyces lanuginosus* DSM 14631$^T$ | Spröer C. et al. (1999), Int J Syst Bacteriol. 49(PT 3): 1255-1262 |
| GU207875 | *Chondromyces pediculatus* DSM 14607$^T$ | This study |
| AJ233942 | *Chondromyces robustus* DSM 14608$^T$ | Spröer C. et al. (1999), Int J Syst Bacteriol. 49(PT 3): 1255-1262 |
| DQ768120 | *Corallococcus coralloides* DSM 2259$^T$ | Park S. et al. (2006), direct submission |
| AJ811598 | *Corallococcus exiguus* DSM 14696$^T$ | Swiderski J. direct submission |
| AJ233921 | *Corallococcus macrosporus* DSM 14697$^T$ | Spröer C. et al. (1999), Int J Syst Bacteriol. 49(PT 3): 1255-1262 |
| DQ768107 | *Cystobacter armeniaca* DSM 14710$^T$ | Park S. et al. (2006), direct submission |
| DQ768108 | *Cystobacter badius* DSM 14723$^T$ | Park S. et al. (2006), direct submission |
| GU207873 | *Cystobacter disciformis* DSM52716T | This study |
| NR 025343 | *Cystobacter ferrugineus* DSM 14716$^T$ | Spröer C. et al. (2008), direct submission |
| DQ768109 | *Cystobacter fuscus* DSM 2262$^T$ | Park S. et al. (2006), direct submission |
| DQ768110 | *Cystobacter gracilis* DSM 14753$^T$ | Park S. et al. (2006), direct submission |
| DQ768111 | *Cystobacter miniatus* DSM 14712$^T$ | Park S. et al. (2006), direct submission |
| DQ768113 | *Cystobacter minus* DSM 14751$^T$ | Park S. et al. (2006), direct submission |
| DQ768115 | *Cystobacter velatus* DSM 14718$^T$ | Park S. et al. (2006), direct submission |
| DQ768114 | *Cystobacter violaceus* DSM 14727$^T$ | Park S. et al., (2006), direct submission |
| NR 024807 | *Enhygromyxa salina* DSM 15217$^T$ | Iizuka T. et al.(2003), Syst Appl Microbiol 26: 189-196 |
| NR 027522 | *Haliangium ochraceum* DSM 14365$^T$ | Iizuka T. et al.(1998), FEMS Microbiol Lett 169: 317-322 |
| NR 024781 | *Haliangium tepidum* DSM 14436$^T$ | Fudou R. et al. (2002), J Gen Appl Microbiol 48: 109-115 |
| AJ233949 | *Hyalangium minutum* DSM 14724$^T$ | Spröer C. et al.(1999), Int J Syst Bacteriol. 49(PT 3): 1255-1262 |
| GU207876 | *Jahnella thaxteri* DSM 14626$^T$ | This study |
| AJ233944 | *Kofleria flava* DSM 14601$^T$ | Spröer C. et al. (1999), Int J Syst Bacteriol. 49(PT 3): 1255-1262 |
| AJ233907 | *Melittangium alboraceum* Me b7$^T$ | Spröer C. et al. (1999), Int J Syst Bacteriol. 49(PT 3): 1255-1262 |
| AJ233908 | *Melittangium boletus* DSM 14713$^T$ | Spröer C. et al. (1999) Int J Syst Bacteriol. 49(PT 3): 1255-1262 |
| GU207877 | *Melittangium lichenicola* DSM 2275$^T$ | This study |
| DQ768117 | *Myxococcus fulvus* DSM 16525$^T$ | Park S. et al. (2006), direct submission |
| DQ768118 | *Myxococcus stipitatus* DSM 14675$^T$ | Park S. et al. (2006), direct submission |
| DQ768119 | *Myxococcus virescens* DSM 2260$^T$ | Park S. et al. (2006), direct submission |
| DQ768116 | *Myxococcus xanthus* DSM 16526$^T$ | Park S. et al. (2006), direct submission |
| AJ233945 | '*Nannocystis aggregans*' DSM14639T | Spröer C. et al. (1999), Int J Syst Bacteriol. 49(PT 3): 1255-1262 |
| AJ233946 | *Nannocystis exedens* DSM 71$^T$ | Spröer C. et al. (1999), Int J Syst Bacteriol. 49(PT 3): 1255-1262 |
| GU207878 | *Nannocystis pusilla* DSM 14622$^T$ | This study |
| EU545827 | *Phaselicystis flava* DSM21295$^T$ | Garcia R. O. et al. (2009), Int J Syst Evol Microbiol. 59(PT12): 1524-1530 |
| NR 024795 | *Plesiocystis pacifica* DSM 14875$^T$ | Iizuka T et al. (2003), Int J Syst Evol Microbiol. 53, 189-195 |
| GU207879 | *Polyangium fumosum* DSM14668$^T$ | This study |
| GU207880 | *Polyangium sorediatum* DSM 14670$^T$ | This study |
| GU207881 | *Polyangium spumosum* DSM 14734$^T$ | This study |
| AJ233909 | *Pyxidicoccus fallax* DSM 14698 T | Spröer C. et al. (1999), Int J Syst Bacteriol. 49(PT 3): 1255-1262 |
| FJ457641 | *Sorangium cellulosum* DSM 14627$^T$ | Youn J. et al. (2008), direct submission |
| EU240498 | '*Sorangium nigrum*' DSM14731$^T$ | Jiang, D. M. et al. (2008), Int J Syst Evol Microbiol. 58 (PT 11): 2654-2659 |

TABLE 1-continued

Reference DNA sequence data used for comparison with the novel myxobacterial
strains of Aetherobacter spp. described in this patent application.

| Accession Number | Myxobacteria Species/Strains | Reference Literature |
| --- | --- | --- |
| GU207882 | *Stigmatella aurantiaca* DSM 17044$^T$ | This study |
| AJ970180 | *Stigmatella erecta* DSM 16858$^T$ | Spröer C. et al. (1999), Int J Syst Bacteriol. 49(PT 3): 1255-1262 |
| DQ768129 | *Stigmatella hybrida* DSM 14722T | Park S. et al. (2006), direct submission |

Production of Omega-3 PUFA, Notably DHA, EPA:

Actively swarming cells from MD1G agar were scraped off from a well-grown agar plate and inoculated into 100 ml flask containing 20 ml MD1G broth. This culture was incubated on a rotary shaker for 7 days at 160 rpm and 30° C. as seed culture. An aliquot of 2 ml taken from the seed culture was introduced into three 250 ml flask containing 50 ml of liquid MD1G medium (i.e., the production medium for fatty acid analysis). Flasks were shaken for ten days at the same speed and temperature as those of the seed culture. Aliquots of 2 ml which contained mainly clumping cells were taken from each flask after five and 10 days of incubation. Wet and dried cell weights were then calculated.

Extraction of the Cellular Fatty Acids:

The cellular fatty acids were extracted using the FAME method [Bode H B et al. (2006) J. Bacteriol 188:6524-6528; Ring M W et al. (2006), J Biol Chem 281:36691-36700 (2006)]. Aliquots (5 μl) of the extracts were analysed by GC-MS.

Identification of cellular fatty acids including EPA and DHA:

Cellular fatty acids including the omega-3 PUFA (EPA and DHA) were identified based on the fragmentation patterns and retention time. These fatty acids (FA) were compared to FAME mix reference standard (Sigma-Aldrich) which contains 37 fatty acid methyl esters. The presence of DHA and EPA were confirmed using reference standards from Sigma-Aldrich (cis-4,7,10,13,16,19-DHA, cis-5,8,11,14,17-EPA)

Quantification of EPA and DHA:

GC-MS was carried out on an Agilent 6890N gas chromatograph with a 5973 electron impact mass selective detector and a 7683B injector (Agilent, Waldbronn, Germany) using a dimethyl-(5% phenyl)-polysiloxane capillary column (Agilent HP-5 ms, 0.25 mm by 30 m by 0.25_m) and helium as the carrier gas at a flow rate of 1 ml/min. Samples were injected in split mode (split ratio, 10:1). The column temperature was kept at 130° C. for 2.5 min, increased to 240° C. at a rate of 5° C./min, and then ramped to 300° C. at 30° C./min and held at 300° C. for 5 min. Other temperatures were as follows: inlet, 275° C.; GC-MS transfer line, 280° C.; ion source, 230° C.; and quadrupole, 150° C. The mass selective detector was operated in scan mode, scanning the mass range from m/z 40 to 500. Data analysis was carried out with AMDIS software, version 2.64 (NIST, Gaithersburg, Md., USA), using the value "integrated signal" for quantification. Amounts were calculated in percentages relative to the sum of integrals of the total fatty acid methyl esters.

DHA and EPA were estimated based on the amount present (2% or 0.2 μg/μl each, respectively) in the reference FAME mixture. An aliquot of 5 μl was taken from the reference mixture and mixed with 95 μl chloroform to give a final volume of 100 μl. From this mixture, an aliquot was injected into the column for GC-MS analysis as specified above.

DHA and EPA were first determined in the FAME mix by analysis of fragmentation pattern and retention time. These peaks areas were then calculated using the integrated signal area which represents the amount present in the standards.

After the cellular fatty acid extracts were analyzed in the GC-MS, peaks corresponding to DHA and EPA were measured using the integrated signal which represents the amount present in the sample (retention time range: EPA 17.5-18.5 min., DHA 20.5-21.5 min).

DHA and EPA amounts were calculated by taking the average of the sample integrated signal divided by the standard integrated signal. It was then multiplied by the concentration of the standard fatty acid and total volume of the fatty acid extract, see the following formula:

$$SFA \times \frac{AIS}{IS} \times TVFAE = \text{mass of desired } PUFAs$$

SFA=Standard FA concentration [mass per volume]
AIS=Average Integrated signal of the sample
IS=Integrated signal of the standard
TVFAE=total volume of FA extract [volume]

The total percentages of polyunsaturated omega-3 PUFAs were finally obtained from the summation of average EPA and DHA. The percentage of cellular fatty acids was determined from the average of triplicate samples.

Maintenance of Strains:

All myxobacterial strains producing omega-3 PUFAs were routinely cultured and maintained in VY/2 agar, where they were found to grow fairly. Long term preservation was carried out in 10% glycerol under liquid nitrogen.

Morphological Observations:

Swarming colonies and fruiting bodies were observed under a Olympus (Hamburg, Germany) SH-ILLB stereoscopic microscope and photographed using Axiocam MRC (Zeiss, Göttingen, Germany) camera. Fruiting bodies were also analysed using laser scanning fluorescent microscope (Zeiss). Vegetative cells and myxospores morphology were studied using a phase-contrast microscope (Zeiss). All growth stages were also observed on VY/2 agar.

Physiological Tests:

Reactions of vegetative cells to Gram and Congo Red stains were determined; staining with the latter was after the method of McCurdy, H. D., Can. J. Microbiol. 15:1453-1461 (1969). Catalase activity was tested with 3% $H_2O_2$. Cellulose degradation was performed on VY/2 and ST21 agar, all overlaid with filter paper (2×1 cm), and in parallel test on Cel-3 agar [Reichenbach H. & Dworkin M (1992) The Myxobacteria, In The Prokaryotes. 2nd edn, pp. 3416-3487 (Balows A et al., eds.) New York: Springer] to determine degradation of cellulose powder. Degradation assay for chitin was done as described by Reichenbach H et al. (2006) Int J Syst Evol Microbiol 56:2357-2363.

Microbial Predation Tests:

Overnight cultures of the gramnegative bacterium *Escherichia coli* were spot-inoculated (ca. 10 mm diameter) on the water agar and air-dried before inoculation of the environmental samples. The culture plates were sealed with parafilm and incubated at 30° C. for 1 week. Clearing of the microbial food baits indicated the lytic action by the spreading myxobacterial colonies.

Growth Responses to Temperature, pH, Carbon & Nitrogen Sources, and Antibiotics:

Tests for growth responses to different levels of temperature and antibiotic resistance were also performed in VY/2 agar. Vegetative cell inocula came from the actively growing swarm taken from the same medium. Antibiotics used were apramycin (Fluka, Buchs, Switzerland), ampicillin, kanamycin, hygromycin B (Roth, Karlsruhe, Germany), tobramycin (Sigma-Aldrich), spectinomycin (Serva, Heidelberg, Germany), tetracycline, oxytetracycline, streptomycin (all from Synopharm, Barsbüttel, Germany), carbenicillin, neomycin, rifampicin and gentamycin (Applichem. Darmstadt, Germany), all filter-sterilized and were added after cooling (50° C.) of the autoclaved medium.

Utilization of nitrogenous compounds was analysed in water agar supplemented with 10 mM of L-aspartic acid, L-glutamic acid, urea, $KNO_3$, and $(NH_4)_2SO_4$. Also tested in the same medium at 0.3% concentration was casamino acid (BD) and different peptone sources [tryptone, casitone, peptone, neopeptone, phytone (BD)].

Carbon source utilization was determined in water agar supplemented with 5 mM HEPES. Final pH was adjusted before autoclaving to 7.0 using KOH. Fructose, D-mannose, saccharose, L-arabinose, D-glucose, D-galactose, sorbitol, cellobiose, soluble starch, molasses, maltose, xylose, and sorbitol were supplemented at concentration of each 0.35%.

G+C Content and 16S rDNA Analysis:

Genomic DNA was extracted from actively growing cells using the protocol for Gram-negative bacteria of the Qiagen Genomic DNA Purification Kit. The DNA G+C content of the novel bacteria was determined by HPLC [Li G et al. (2003) Bio Techniques 34:908-909 (2003); Shimelis O & Giese R (2006) J. Chrom. 1117:132-136]. The 16S rDNA analysis was performed according to Garcia R O et al. (2009) Int J Syst Evol Microbiol 50(PT12):1524-1530. The obtained 16S rDNA sequences were also compared to the NCBI-BLAST nucleotide-nucleotide data bank. This service is provided by the National Center for Biotechnology Information (NCBI) located at the U.S. National Library of Medicine 8600, Rockville Pike, Bethesda Md., 20894 USA as Basic Local Alignment Search Tool (BLAST). In particular the Nucleotide database (BLASTn) was searched.

EXAMPLES

Example 1: Production of Fatty Acids by the Strains of the Invention

*Aetherobacter fasciculatus* DSM 21835, *Aetherobacter rufus* DSM 23122 and *Aetherobacter* sp. DSM 23098

A. Production of Omega-3 PUFA (DHA, EPA):

From actively swarming cells on surface of MD1 G agar culture, *Aetherobacter fasciculatus* DSM 21835, *A. rufus* DSM 23122 and *Aetherobacter* sp. DSM 23098 grew as clumps on MD1G liquid culture. This condition made it impossible to quantify the cells by optical density. Cells harvested on the fifth day of shaken culture showed yellowish color which were microscopically revealed as long slender rods (vegetative cells). On the tenth day of growth, cells became red which after microscopic examination revealed structures, which presumably represent fruiting bodies (FIG. 1a). They contain enclosing walls (sporangioles) which contain spores inside and shows similarity to fruiting bodies found on surface of the agar (FIG. 1b). The vegetative cells seem responsible for the yellowish mass and were presumably converted to spores after 10 days of incubation. This event was only observed in *A. fasciculatus* DSM 21835.

Both strains grew well if inoculated in 1 l flasks containing 750 ml MD1G which was inoculated with 50 ml seed culture, but more clumpy cell pellets were produced, and cells were not converted to fruiting bodies even after 10 or more days of incubation.

The observation that better growth in high-volume medium presumably reflects the nature of both strains to burrow under the agar which suggests a lesser demand for air might be required for growth. In addition, the weak catalase reaction observed would also support this hypothesis. Analysis of these data implied that all *Aetherobacter* strains are potentially microaerophilic or facultative aerobic. This basic information appears important in the cultivation of the strain and consequently for the analysis of PUFA production.

Tables 2-7 show the triplicate cell weight measurements of *Aetherobacter fasciculatus* DSM 21835, *A. rufus* DSM 23122 and *Aetherobacter* sp. DSM 23098 taken after 5 and 10 days of cultivation, respectively, in MD1G shake flasks. DHA and EPA peaks were measured from triplicate samples using the integrated signal.

TABLE 2

Production of EPA and DHA in *Aetherobacter fasciculatus* DSM 21835 as determined by GC-MS

| | Incubation | | | | | | | |
|---|---|---|---|---|---|---|---|---|
| | 5 days | | | | 10 days | | | |
| | Cell weight (mg) | | Integrated Signal | | Cell weight (mg) | | Integrated Signal | |
| Replicate | wet wt (2 ml) | dry wt | EPA | DHA | wet wt (2 ml) | dry wt | EPA | DHA |
| 1 | 12.60 | 1.15 | 1814856 | 4576438 | 6.75 | 1.05 | 779905 | 956110 |
| 2 | 8.50 | 1.00 | 2143276 | 6005853 | 8.35 | 1.35 | 104431 | 79625 |
| 3 | 4.75 | 1.15 | 1013666 | 2686956 | 6.85 | 0.90 | 1870499 | 1833352 |
| Ave. | 8.62 | 1.10 | 1657266 | 4423082.33 | 7.32 | 1.10 | 918278.33 | 956362.33 |
| Production in 5-days (µg) | | | 10.96 | 25.13 | Production in 10-days (µg) | | 6.07 | 5.43 |

TABLE 3

Production of EPA and DHA in *Aetherobacter rufus* DSM 23122

| | Incubation | | | | | | | |
|---|---|---|---|---|---|---|---|---|
| | 5 days | | | | 10 days | | | |
| | Cell weight (mg) | | Integrated Signal | | Cell weight (mg) | | Integrated Signal | |
| Replicate | wet wt (2 ml) | dry wt | EPA | DHA | wet wt (2 ml) | dry wt | EPA | DHA |
| 1 | 8.85 | 8.60 | 81834 | 307959 | 9.75 | 9.60 | 50035 | 72329 |
| 2 | 9.85 | 9.55 | 120330 | 254265 | 10.00 | 9.65 | 86108 | 122422 |
| 3 | 11.5 | 11.10 | 48063 | 148092 | 8.85 | 8.50 | 89127 | 167611 |
| Ave. | 10.06 | 9.75 | 83409 | 236772 | 9.53 | 9.25 | 75090 | 120787 |
| Production in 5-days (µg) | | | 0.55 | 1.35 | Production in 10-days (µg) | | 0.50 | 0.69 |

TABLE 4

Production of EPA and DHA in Aetherobacter sp. DSM 23098

| | Incubation | | | | | | | |
|---|---|---|---|---|---|---|---|---|
| | 5 days | | | | 10 days | | | |
| | Cell weight (mg) | | Integrated Signal | | Cell weight (mg) | | Integrated Signal | |
| Replicate | wet wt (2 ml) | dry wt | EPA | DHA | wet wt (2 ml) | dry wt | EPA | DHA |
| 1 | 91.70 | 5.20 | 1523968 | 1168505 | 52.30 | 4.20 | 817217 | 681803 |
| 2 | 75.53 | 4.00 | 9551819 | 8726014 | 39.10 | 3.30 | 858006 | 786250 |
| 3 | 116.4 | 7.90 | 1729513 | 1571913.7 | 44.40 | 4.30 | 856852 | 847829 |
| Ave. | 94.54 | 5.7 | 4268433 | 3822144 | 45.27 | 3.93 | 844025 | 771961 |
| Production in 5-days (µg) | | | 40.34 | 43.41 | Production in 10-days (µg) | | 7.98 | 8.77 |

Figure 2:
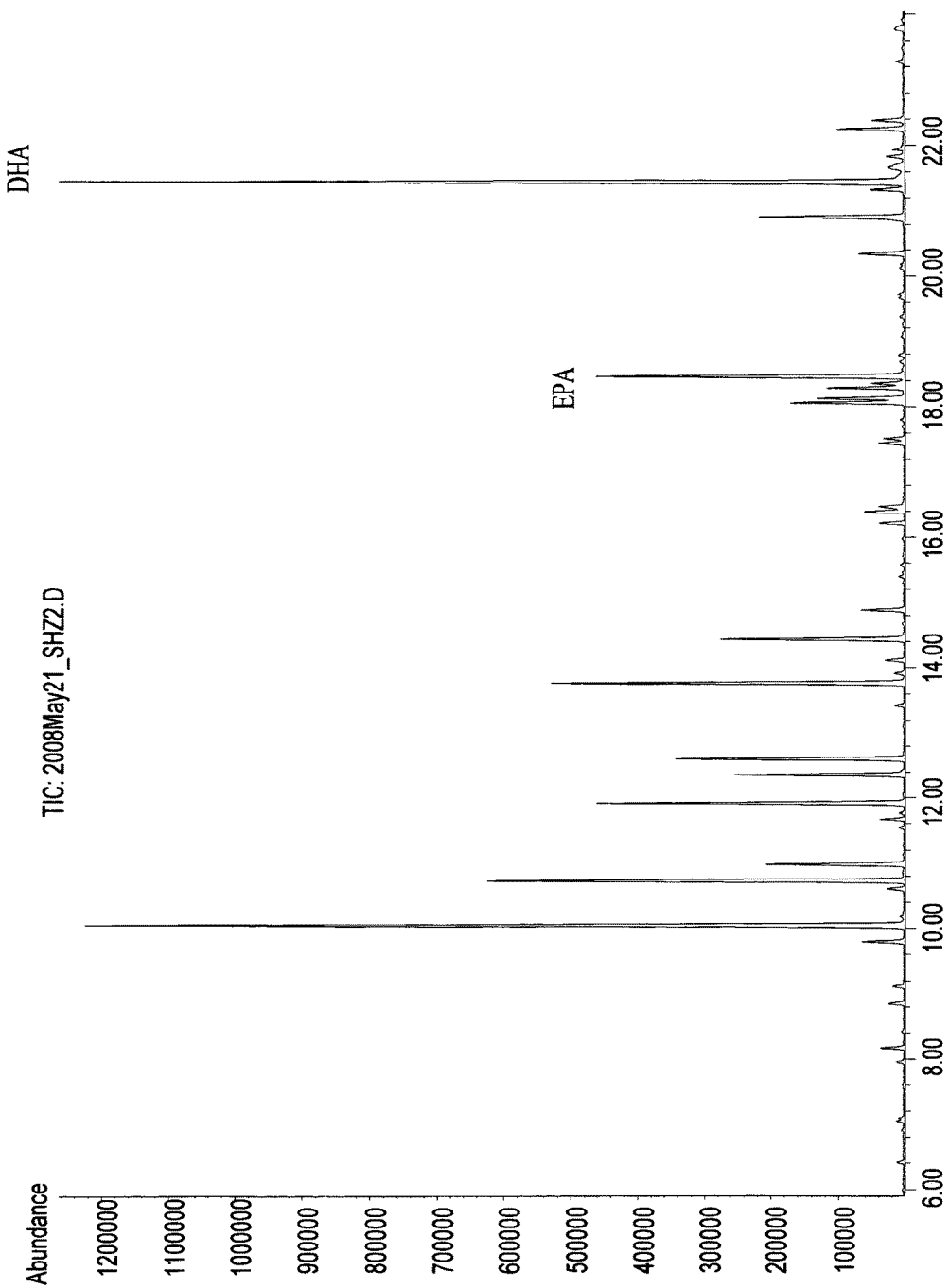
FIG. 2: GC-MS chromatograms of *Aetherobacter fasciculatus* DSM 21835 cellular fatty acids extracted from triplicate samples of 5 day culture

FIG. 2 shows the GC-MS chromatogram of the fatty acid containing extract taken after 5 days of fermentation in MD1G medium. Strains DSM 23122 and DSM 23098 yielded comparable, but slightly lower amounts of DHA and EPA (see Tables 3 and 4).

B. Identification of Cellular Fatty Acids Including EPA and DHA:

FIG. 2 shows the GC-MS chromatogram of *A. fasciculatus* DSM 21835 cellular fatty acids. In the tables 5-7 the corresponding percentages of the fatty acids extracted from 5$^{th}$ and 10$^{th}$ day of incubations are presented.

TABLE 5

Percentages of cellular fatty acids of *Aetherobacter fasciculatus* DSM 21835

| Fatty Acids | Average of triplicates after 5 days | Average of triplicates after 10 days |
|---|---|---|
| iso13:0 | 0.07 | 0.31 |
| 13:00 | 0.04 | 0.16 |
| iso14:0 | 0.49 | 1.21 |
| 14:00 | 0.21 | 0.13 |
| iso15:0 | 16.44 | 21.62 |
| aiso15:0 | 0.01 | 0.56 |
| 15:1 isomer | 0.20 | 0.13 |
| 15:00 | 5.23 | 5.64 |
| iso16:0 | 5.93 | 5.38 |
| 16:1w5c | 2.94 | 2.26 |
| 16:00 | 3.93 | 2.50 |
| iso17:1w5c | 0.19 | 0.14 |
| iso17:0 | 6.80 | 8.74 |
| aiso17:0 | 8.32 | 2.99 |
| 16:0 9,10CH2 | 0.42 | 0.39 |
| 17:00 | 3.95 | 6.32 |

TABLE 5-continued

Percentages of cellular fatty acids of *Aetherobacter fasciculatus* DSM 21835

| Fatty Acids | Average of triplicates after 5 days | Average of triplicates after 10 days |
|---|---|---|
| iso18:0 | 0.08 | 0.06 |
| 18:00 | 0.61 | 0.27 |
| 16:0 2OH | 0.75 | 0.09 |
| unknown | 0.58 | 0.16 |
| iso17:0 2OH | 0.56 | 0.09 |
| 17:1 2OH | 0.55 | 0.27 |
| 17:0 2OH | 2.58 | 1.21 |
| 17:0 2OH isomer | 2.71 | 3.19 |
| ARA | 0.64 | 0.42 |
| 20:5 (EPA) | 6.99 | 8.35 |
| 22:6 (DHA) | 18.90 | 8.64 |
| unknown PUFA | 0.26 | 0.08 |
| unknown3 | 1.68 | 2.66 |
| OAG | 3.67 | 8.56 |
| OAG | 0.46 | 0.26 |
| OAG | 0.99 | 1.10 |
| OAG | 1.68 | 2.66 |
| OAG | 1.11 | 3.48 |
| Total | 100.00 | 100.00 |

TABLE 6

Percentages of cellular fatty acids of *Aetherobacter rufus* DSM 23122

| Fatty Acids | Average of triplicates after 5 days | Average of triplicates after 10 days |
|---|---|---|
| Iso13:0 | 0.08 | n.d. |
| 13:00 | 0.20 | n.d. |
| Iso14:0 | 0.13 | 0.07 |
| 14:00 | 1.23 | 0.71 |
| Iso15:0 | 23.90 | 21.34 |
| aiso15:0 | 0.30 | n.d. |
| 15:1 isomer | 0.19 | n.d. |
| 15:00 | 8.88 | 4.21 |
| iso16:0 | 1.76 | 2.10 |
| 16:1w5c | 5.19 | 5.36 |
| 16:00 | 8.65 | 6.83 |
| iso17:0 | 3.12 | 2.48 |
| 16:0 9,10CH2 | 0.13 | n.d. |
| 17:00 | 3.64 | 3.85 |
| 18:00 | 7.04 | 10.44 |
| 16:0 2OH | 0.36 | 0.23 |
| unknown | 0.67 | 1.39 |
| iso17:0 2OH | 0.07 | n.d. |
| 17:1 2OHpotential | 4.08 | 12.39 |
| 17:1 2OH | 0.18 | 0.30 |
| 17:0 2OH | 2.61 | 2.31 |
| Unknown2 | 1.28 | 0.91 |
| 20:5 (EPA) | 3.95 | 5.59 |
| 22:6 (DHA) | 14.96 | 8.70 |
| Unknown3 | 3.31 | 5.14 |
| i15:0 OAG | 1.64 | 1.48 |
| unknown OAG | 2.47 | 4.16 |
| Total | 100.00 | 100.00 |

TABLE 7

Percentages of cellular fatty acids of *Aetherobacter* sp strain DSM 23098.

| Fatty Acids | Average of triplicates after 5 days | Average of triplicates after 10 days |
|---|---|---|
| iso-13:0 | 0.08 | 0.06 |
| 13:0 | 0.08 | 0.08 |
| 14:0 | 0.20 | 0.29 |
| iso-15:0 | 23.17 | 21.69 |
| 15:1 Isomer 2 | 0.17 | n.d. |
| 15:0 ME | 1.86 | 1.17 |
| iso-15:0 DMA | 9.40 | 11.81 |
| 16:1w5c | 2.82 | 1.08 |
| 16:0 | 2.14 | 3.10 |
| iso-17:1w5c | 0.10 | n.d. |
| iso-17:0 | 2.05 | 2.14 |
| 16:0 9,10-CH2 | 0.42 | n.d. |
| 17:0 | 1.31 | 1.14 |
| 18:3 | 0.09 | n.d. |
| 18:0 | 1.43 | 2.60 |
| 16:0 2-OH | 0.51 | 0.43 |
| iso-17:0 2-OH | 0.35 | 0.46 |
| 17:1 2-OH | 0.84 | 1.68 |
| 17:1 2-OH | 12.94 | 22.95 |
| 20:4w6,9,12,15 all cis | 1.47 | 0.90 |
| 20:5w3,6,9,12,15 all cis | 10.90 | 5.62 |
| 22:6w3,6,9,12,15,18 all cis | 9.49 | 5.12 |
| iso-15:0 OAG | 1.81 | 1.85 |
| 15:0 OAG | 10.21 | 10.17 |
| 16:1 OAG | 4.86 | 4.23 |
| 16:0 OAG | 1.85 | 1.41 |
| Total | 100.00 | 100.00 |

Cellular fatty acids were identified as described above in the chapter general methods and materials.

Figure 3:
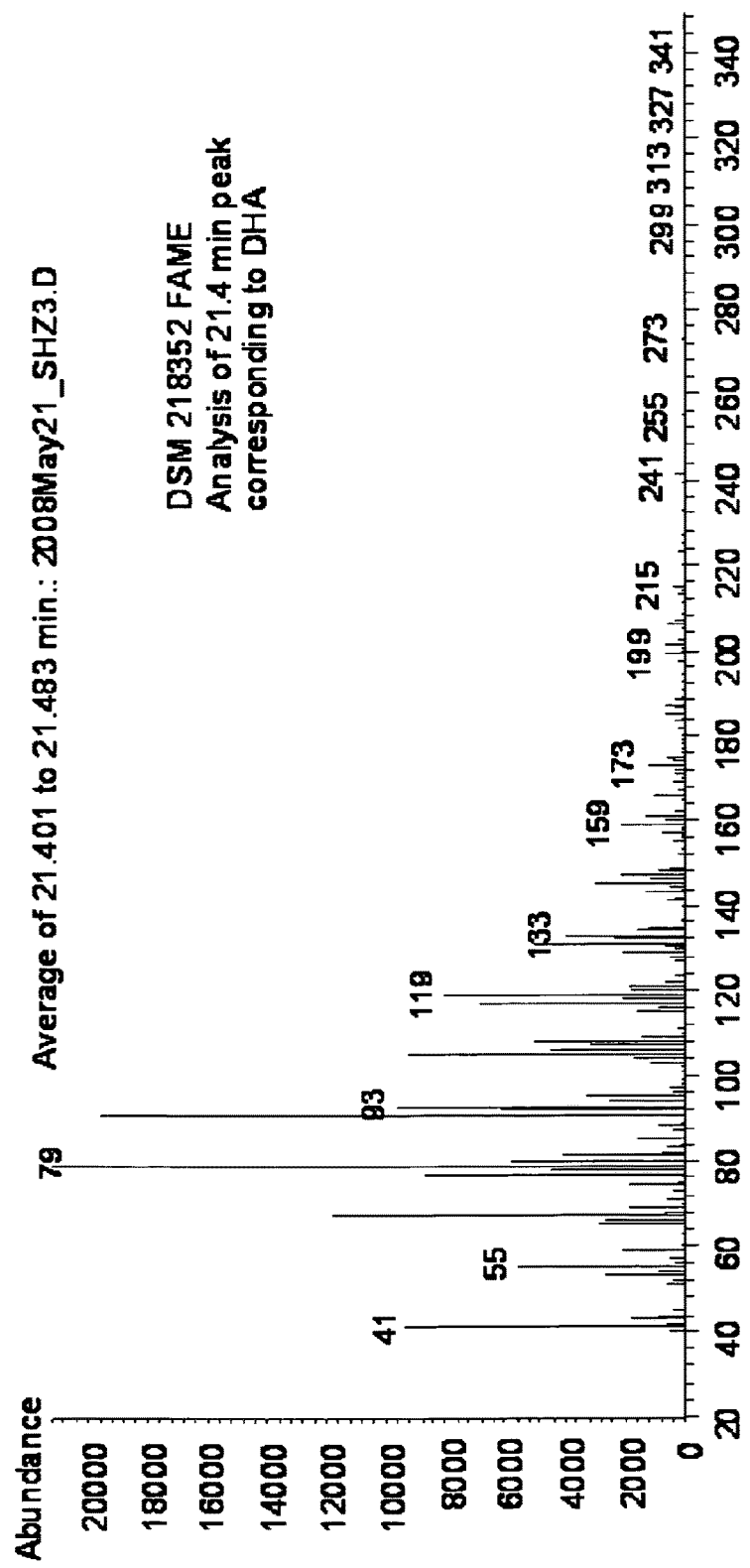
FIG. 3: Fragmentation pattern of DHA,
upper line: representative culture sample of *Aetherobacter fasciculatus* DSM 21835 lower line: purchased reference of DHA methyl ester
Figure 4:
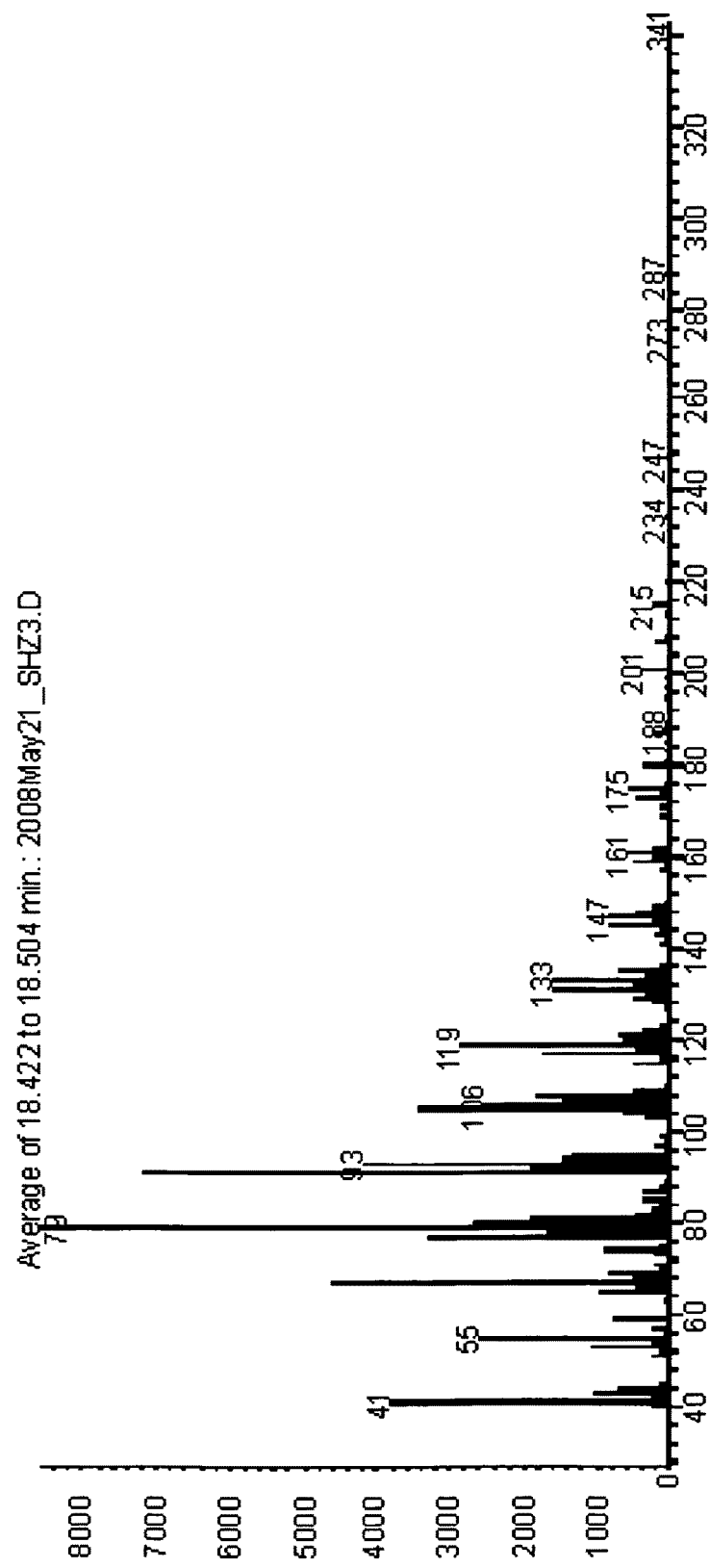
FIG. 4: Fragmentation pattern of EPA,
upper line: representative culture sample of *Aetherobacter fasciculatus* DSM 21835 lower line: purchased reference of EPA methyl ester

Fragmentation pattern of the samples revealed the identity of the mass units to the standard methyl esters of DHA and EPA as outlined exemplarily in FIGS. 3 and 4 for strein *A. fasciculatus* DSM 21835.

C. Extraction and Quantification of the Cellular Fatty Acids:

As presented in the tables 2-7 all three strains contain at least 15% total PUFAs (EPA and DHA taken together) of dry cell mass. The highest observed amount was more than 25%. The data further indicate that optimum production will be reached within the period of 10 days.

Example 2: Identification of Strain *A. fasciculatus* DSM 21835

Strain DSM 21835 was isolated in November 2007 from an Indonesian soil sample containing pieces of roots and other decaying plant materials. The strain was discovered because it formed yellowish-orange fruiting bodies growing in bacterial bait on the surface of buffered water agar. Morphological observations under the dissecting microscope revealed clusters of sporangioles packed into sod. Inoculation of the washed fruiting body material onto fresh VY/2 agar led to production of a thin and delicate swarm that coherently migrated on the surface and inner part of the agar. A series of repetitive transfers of the swarming material lead to the isolation of the pure strain.

Morphological and Cultural Characteristics:

Swarm: On VY/2 agar bacterial colonies or swarms typically spread under producing a curtain-like appearance (FIG. 1b). Cell densities are higher at the edge of the swarm. Migrating cells move coherently while at the same time clearing the yeast cells. Cells may also spread coherently on surface of the agar and exhibit shallow degradation. In water agar baited with live *Escherichia coli*, the swarm colony spreads thinly on the surface of the agar to produce long and fine radiating veins. In MD1 agar, the bacteria hardly spread over the surface and usually tend to grow deeply especially on the site of inoculation. A yellowish-cream coloured colony is typically formed in this medium with characteristic agar depressions. A thin and film-like swarm architecture appears on this agar.

Vegetative cells: The vegetative cells in slide mounts are long and slender rods, measuring 1.2-1.3×2.9-5.7 μm (FIG. 1a), with rounded ends as typical for suborder Sorangiineae. Dark spot granules are present on the polar ends of the cells, which are clearly visible under the phase-contrast microscope. Motility occurs by gliding under and on the surface of the agar. Vegetative cells aggregate to produce yellowish pigments during shake flask fermentations in MD1G medium.

Fruiting bodies: On VY/2 agar, fruiting bodies are composed of sporangioles which are packed in bundles or sori that are commonly arranged in a cluster or chained fashion (FIG. 1c). Normally they develop after 2 weeks of incubation. Fruiting bodies are commonly produced on the edge of the swarm and under the agar. Sometimes during the fruiting body development, a yellow diffusible pigment is observed. The sporangioles are spherical to oval in shape and measures 10.4×11.4 μm. A typical sorus measures 30×50 μm and contains 5-20 tiny sporangioles. A clear, glistening and transparent slime is often found enclosing the fruiting bodies on surface of the VY/2 agar.

Myxospores: Crushed sporangioles release tightly packed, optically refractive rod cells which are presumably myxospores (FIG. 1d). Those are shorter and nearly as wide as the vegetative cells (1.0-1.2×3.2-4.0 µm), and with more or less rounded ends.

Physiological Characteristics

Staining, degradation, and lytic properties: Vegetative cells are Gram-negative and catalase-positive. The swarm colony remains unstained with Congo Red, as typical for Sorangiineae. Live bacterial food bait (E. coli) on water agar is completely degraded and cleared after 6 days of incubation at room temperature, suggesting strongly bacteriolytic properties. The strain is unable to degrade cellulose on Cel-3 agar and ST21 agar overlaid with filter paper, and chitin powder on CT-7 agar is not degraded either. Agar degradation is commonly observed in cultures grown in VY/2 and MD1 agar.

Growth responses to temperature and pH. On yeast agar, the growth optimum is observed at 30° C. incubation, but fair growth is still attained at 18° C. on the same agar. No growth occurred at 37° C. In the same medium, the strain can grow in the range of pH 5-9 with the largest swarm diameter becoming evident at pH 7.0. However, no evidence of growth is found at pH below 4.0 and above pH 10.

Utilisation of carbon sources. The best carbon source to support growth of the strain is lactose. Fair growth is also observed in molasses, maltose, and xylose; moderate growth on saccharose, fructose, D-mannose, L-arabinose, galactose, sorbitol, mannose, and glucose. Cellobiose and poor growth on soluble starch. Fruiting bodies could be seen in the presence of monosaccharide sugars (e.g. glucose, mannose) and sorbitol.

Utilisation of nitrogen sources The largest swarm colony diameter is attained with glutamic acid, potassium nitrate, and aspartic acid. Urea and ammonium sulfate only allow for poor growth, resulting in rather thin and scattered swarms. Among complex nitrogen sources, Casitone, Peptone, and Neopeptone are best suited; tryptone and phytone still exhibit fair growth, but the strain grows only poorly on casamino acids.

Antibiotic resistance: The strain is sensitive to kanamycin, spectinomycin, tetracycline, oxytetracycline, carbenicillin, and rifampicin. Resistance is observed against gentamycin, apramycin, tobramycin, streptomycin, ampicillin, neomycin and hygromycin B.

Mol % G+C Analysis The DNA G+C content of the is 68.9 mol %

Example 3: Identification of *Aetherobacter rufus* Strain DSM23122

The myxobacterial strain DSM23122 was isolated in November 2007 from an Indonesian soil sample containing pieces of roots and other decaying plant materials. The sample had originally been collected in 1962 and preserved at the Zentrum für Biodokumentation, Landsweiler-Reden, Germany. The soil was processed for isolation using standard baiting methods [Reichenbach H & Dworkin M (1992) The Myxobacteria, In The Prokaryotes, 2nd edn, pp. 3416-3487 (Balows A et al., eds) New York: Springer]. The strain was noticed by the reddish-colour of its fruiting bodies on the surface of the filter paper on mineral salts agar [Shimkets et al., 2006. The myxobacteria. In The Prokaryotes: a Handbook on the Biology of Bacteria, 3rd edn, vol. 7, pp. 31-115 (Dworkin M et al., eds) New York: Springer]. Inoculation of the fruiting body onto the same fresh medium resulted in the appearance of a thin and delicate, swarm which coherently migrates on surface of the agar. The strain was isolated to purity after repetitive transfer of the swarming material onto new culture media.

Morphological and Cultural Characteristics:

Swarm. On solid VY/2 medium (FIG. 1f) the bacterial colonies or swarms typically spread on the surface and under the agar. Higher cell densities are observed at the edge of the swarm, visible as white band. Migrating cells move coherently while clearing the autoclaved yeast cells. The swarming on the surface of the agar exhibits a shallow degradation. In water agar baited with live E. coli, the swarm spreads thinly and transparently, sometimes producing long and fine radiating veins. Upon contact with the bait, a wave- or ridge-like swarm-edge architecture is produced. The bait bacteria are completely degraded after 2-3 days of incubation.

Vegetative cells. The vegetative cells (FIG. 1e) are long, slender rods measuring 1.1-1.2×3.0-7.0 µm, with rounded ends as typical for suborder Sorangiineae. Dark spot granules are present on the polar ends of the cells, as revealed by phase-contrast microscopy. Motility is accomplished by gliding on the surface of the agar and under the agar. Vegetative cell pellets remain whitish in liquid MD1 medium.

Fruiting bodies. Completely developed fruiting bodies were observed after two weeks of incubation. In VY/2 and water agar, fruiting bodies (FIG. 1g) are composed of a reddish mass measuring 375×650 µm-425×1400 µm which are usually visible to the naked eye. Under brightfield and phase-contrast microscope, these masses are revealed to be composed of tiny and compact sporangioles. Normally they start to develop as white aggregation of vegetative cells after a week of incubation. Typically the fruiting bodies are located on surface of the agar, commonly at the edge of the swarm, but sometimes fructification takes place under the agar, resulting in morphologically similar structures. A single sporangiole (4.0×7.0 µm) measures almost twice the length of a single Cystobacteraceae vegetative cell.

Myxospores. Crushed sporangioles release tightly packed, slightly optically refractive rod cells which are presumably myxospores (FIG. 1h). Those are short and nearly as wide as the vegetative cells (1.0×2.0 µm-1.1×3.0 µm), and with rounded ends.

Physiological Characteristics

Staining and lytic properties. The swarm colony remains unstained with Congo red, as typical for Sorangiineae; Vegetative cells are Gram-negative and catalase-positive. The strain differed from related genera by its inability to degrade cellulose powder on Cel-3 and filter paper on ST21 agar. Chitin powder on CT-7 agar was, also not degraded. Partial agar degradation was commonly observed on VY/2 and MD1 agar.

Growth responses to temperature and pH. On yeast agar, the growth optimum is observed at 30° C. incubation, but fair growth is still attained at 18° C. on the same agar. No growth occurred at 37° C. In the same medium, growth is observed in the range of pH 5-8 with pH 7.0 being optimal. No evidence of growth is found at pH 4.0 and below and pH 9.0 and above.

Utilisation of carbon sources. All carbon sources tested were equally utilised.

Utilisation of nitrogen sources. The largest swarm colony diameter is attained with glutamic acid, aspartic acid, ammonium sulfate and potassium nitrate, while the strain grows poorly in urea. Among complex nitrogen sources, casitone shows the optimal growth; peptone, neopeptone and tryptone still exhibited fair growth, phytone exhibits only poor growth, and no growth at all is observed with casamino acids.

Antibiotic resistance. The strain is resistant to gentamycin, ampicillin and neomycin. Sensitivity was observed to apramycin, tobramycin, kanamycin, spectinomycin, hygromycin B, tetracycline, oxytetracycline, streptomycin, carbenicillin, and rifampicin.

Mol % G+C Analysis. The DNA G+C content is 68.0 mol %.

Example 4: Identification of *Aetherobacter* sp. Strain DSM 23098

Strain DSM 23098 was isolated in February 2009 from an Indonesian soil sample. The sample had originally been collected in 1962 and preserved at the Zentrum für Biodokumentation, Landsweiler-Reden, Germany. The soil was processed for isolation using live bait *Escherichia coli* according to the described method [Shimkets et al., 2006. The myxobacteria. In The Prokaryotes: a Handbook on the Biology of Bacteria, 3rd edn, vol. 7, pp. 31-115 (Dworkin M et al., eds) New York: Springer]. The bacterium was recognized for its almost transparent colony forming independent swarms on the surface of the agar and islated to purity by repetitive transfer onto new culture media.

Morphological and Cultural Characteristics

Swarm. In yeast medium (VY/2), the colonies (FIG. 1k) spread almost transparently along the centre of the swarm. A ring appears at the edges of well-grown colonies. The enlarging ring colony is more evident at lower agar concentration (e.g. 8-10 g/l Agar), and usually shows an orange colour around the edges. Incubation under light may cause a stronger pigmentation and leads to a darker, orange colour of the swarm. Migrating cells move coherently while at the same time lysing the autoclaved yeast cells, resulting in the partial to total clearance of the agar medium. Swarming on the surface of the yeast agar exhibits shallow depressions; however this may also become deeper at reduced agar concentration. In water agar baited with live *E. coli*, the swarm spreads thinly and almost transparently. The edges typically show wave-like patterns on the agar surface. Sometimes short and fine ripples are also seen on the surface of the agar. Upon contact with foreign bacteria, a wave- or ridge-like architecture of the colony is produced, as in most bacteriolytic myxobacteria. The vegetative cells usually die after reaching the edge of the agar plate culture, as commonly observed in myxobacteria. Under starving and unfavourable conditions, migrating cells or swarm undergo fruiting body development.

Vegetative cells. The vegetative cells (FIG. 1i) are long, slender, and phase dark rods, measuring 1.1-1.2×3.0-11.0 µm (but mostly only 6-7 µm long) with rounded ends as typically found in the suborder Sorangiineae. Motility was by gliding on the surface and within the agar. When grown in liquid culture, a yellow to light orange colour of the vegetative cell pellet was produced, similar to that on the agar surface during the mound formation of fruiting body development.

Fruiting bodies. In VY/2 agar, the fruiting bodies (FIG. 1l) are composed of sporangioles that usually are visible as orange spots, typically located within the agar. Sometimes, a transparent slime surrounding the fruiting body is observed on the agar surface, similar as in *A. fasciculatus*. Fruiting body development starts from aggregated mass of vegetative cells appearing as yellow to light orange mounds. The sporangioles are composed of bundles measuring 30×37 µm-125×67.5 µm. These bundles contain 3-9 oval to spherical sporangioles of 8×7-17×15 µm size.

Myxospores: Crushed sporangioles release tightly packed and slightly optically refractive rod cells which are presumably myxospores (FIG. 1m). Those are slightly shorter and nearly as wide asthose of the vegetative cells (1.0-1.2 µm×3.0-5.0 µm), and with rounded ends. This characteristic matched to the suborder Sorangiineae.

Physiological Characteristics

Staining and lytic properties: The vegetative cells are Gram-negative and catalase-positive. The swarm colony remains unstained with Congo red, as in other Sorangiineae. The strain differed from related cellulose degrading genera by its inability to degrade cellulose powder on Cel-3 and filter paper on ST21 agar. Chitin powder on CT-7 agar was also not degraded by the swarming cells. Shallow agar depression are also be seen in most solid culture media, indicating that the strain is able to degrade agar as well.

Microbial predation test: The baited bacterium was cleared out in the course of 5-7 days incubation at 30° C., suggesting bacteriolytic activity.

Growth responses to temperature and pH: On yeast agar, fair growth is attained in a range from 18-30° C., but no growth occurred at 37° C. In the same medium, growth was observed within a range from pH 6-8, with the largest swarm diameter observed at pH 7.0.

Utilisation of carbon sources: None of the tested carbon sources except for soluble starch, supported well the growth of the strain.

Utilisation of nitrogen sources: Growth is poor in all tested inorganic nitrogen sources Among different complex organic nitrogen sources, tryptone is suited best. However, the strain also grows well in peptone, neopeptone and casitone; and even phytone and casamino acids were comparably better suited than inorganic nitrogen sources.

Antibiotic resistance. The strain is sensitive to all antibiotics tested except for tobramycin and hygromycin B.

Example 5: Comparative Studies of PUFA Production in Myxobacteria

To establish correlations between taxonomy and phylogeny in the one hand and production of omega-3 PUFAs on the other hand, a series of type strains and other well-characterised representatives from various taxonomic groups of myxobacterial and allied gliding bacteria were studied for comparison for production of DHA, EPA and other fatty acids. The majority of these strains are listed in Table 1, their 16S rDNA sequences were also taken for the phylogenetic study (Example 6). In addition, some further strains from the SB collection were also studied for FA profiles by GC-MS, which were morphologically in agreement with *Sorangium cellulosum* but so far not included in the molecular phylogeny.

For this purpose, authentic and type strains of various myxobacteria and related phylogenetic groups were obtained from DSMZ (Braunschweig; Germany), the Helmholtz Center for Infectious Diseases (HZI, dto.) or from the culture collection of Universität des Saarlandes (Saarbrücken, Germany; SB). Most bacteria were cultivated as shake cultures in 300 ml Erlenmeyer flasks containing 50 ml of the respective culture media (as specified below) at 170 rpm. The incubation temperature was 30° C., except for *Haliangium tepidum* (which was incubated at 37° C.). Members of the genera *Polyangium, Chondromyces, Jahnella*, and *Byssovorax* were cultivated in VY/2 medium, to which maltose was added in case of *Byssovorax*, following the protocol proposed by Kunze B et al. (2006) J Antibiotics 59:664-668. Species of *Archangium, Corallococcus, Hyalangium, Kofleria, Melittangium, Myxococcus, Nannocystis, Pyxidicoccus, Stigmatella* and *Angiococcus* (presently classified in *Cystobacter*), as well as *Cystobacter armeniaca* and *C. disciformis*, were cultivated in MD1 medium (Shimkets et al, 2006). All other *Cystobacter* spp. were grown in M-med [Müller R & Gerth K (2006) J Biotechnol 121:192-200], and HS medium [Kopp M et al (2004) J Biotechnol 107:29-40] was used for *Sorangium* species. Marine myxobacteria belonging to *Enhygromyxa* and *Plesiocystis* were grown in VY/4-SWS [Iizuka T et al. (2003a) Int J Syst Evol Microbiol 53:189-195; Iizuka T et al. (2003b) Syst Appl Microbiol 26:189-196], while *Haliangium* was cultivated in CY-SWS [Iizuka T et al. (1998) FEMS Microbiol Lett 169:317-322]. Fatty acid profiles of *Phaselicystis flava* were taken from Garcia R O et al. (2009) Int J Syst Evol Microbiol 59:1524-1530: Gliding bacteria belonging to *Herpetosiphon* were obtained from HZI, and *Flexibacter* from SB. The later bacteria were cultivated in LB medium, while *Herpetosiphon* strains were grown on a solid VY/2 agar medium.

Extraction of Fatty Acids for Analyses

For the majority of strains, cell pellets were obtained from 2 ml liquid culture aliquots of the shake cultures, which were completely dried at 60° C. for 30 min in a vacuum centrifuge. In case of *Herpetosiphon* spp., which did not grow in liquid medium, a loopful of cells were scraped off from the surface of the agar of well-grown solid media.

Dried cells were then extracted overnight with 500 uL FAME solution (methanol, toluene, sulfuric acid; 50:50:2 v/v). Thereafter, an aliquot of 400 uL R2 reagent (0.5 M NH4HCO3, 2 M KCl) was added. After mixing the sample in a vortex, the solution was centrifuged at 5000 rpm for 4 min and 75 ul extract taken from the upper phase of the solution were derivatized with 25 ul MSTFA. The sample was then incubated at 37° C. for 30 min before being subjected to GC-MS analysis.

Results are depicted in tables 8 and 9, revealing large amounts of EPA and DHA are particularly restricted to the members of the new genus *Aetherobacter*. Various groups of Myxobacteria showed no production of omega-3-PUFA at all. Among other *Sorangiiinae*, all type strains studied were found devoid of omega-3 PUFAs. Surprisingly, two recently isolated strains of *Sorangium cellulosum* from the SB collection show the general morphological and physiological characteristics of the genus and species, revealed production of EPA in small amounts when studied by GC-MS as shown in table 8. This observation gives rise to assume that a closer examination of further *Sorangium* spp. and other species of suborder Sorangiineae will inadvertently reveal additional producer strains for these omega-3 PUFAs.

In the type strain of the marine species *Enhygromyxa salina* (suborder Nannocystineae), EPA was also found in small amounts (table 9), revealing the general potential of this suborder to produce omega-3 PUFAs. The said compounds were not encountered in the gliding non-fruiting eubacteria (*Flexibacter, Herpetosiphon*) studied concurrently, and they were not found in any of the other taxa of grampositive and gramnegative eubacteria that have so far been widely studied for their fatty acid profiles in the course of chemotaxonomic studies, except for the examples cited above in "State of the Art." Even the discovery of EPA in *Enhygromyxa* and *Sorangium* has never before reported, possibly owing to the fact that only the major FA components of bacteria were so far regarded during their chemotaxonomic evaluation by GC-MS. Myxobacteria therefore remain the only class of eubacteria that has many species that can be easily cultured and produce significant amounts of the commercially valuable omega-3 PUFA (i.e., DHA and EPA) at the same time, as discovered in the course of this study. Using a modification of the well-established chemotaxonomic technique for FA-profiling by GC-MS with special emphasis on DHA and EPA has lead in our study to the identification of additional producers of these compounds. From these data it is concluded that certain taxa of Myxobacteria differ from the remainder of culturable eubacteria by having the ability to produce omega-3 PUFA. As up to 90% of all existing eubacterial species remain to be discovered and described, the chances are good to find additional producers, in addition to the novel genus *Aetherobacter* that can also produce omega-3 PUFAs. A novel strategy, including phylogenetic and chemotaxonomic data, following the examples provided in this patent application, is therefore proposed to discover additional myxobacterial producers of omega-3 PUFAs.

TABLE 8

Distribution of fatty acids in strains of *Soranium cellulosum* (SB collection).

| Fatty acids [%] Straight-chain | Strain SBSo021 | SBSo024 |
|---|---|---|
| C14:0 | 2.36 | 1.38 |
| C14:1w5cis | 0.10 | |
| C15:0 | | |
| C16:0 | 19.03 | 17.36 |
| C16:1w5c | 19.34 | 7.45 |
| C16:1w9c | | 0.07 |
| C16:2 | | 0.15 |
| C17:0 | 0.71 | 0.07 |
| C18:0 | 2.83 | 7.14 |
| C18:1 | | 0.41 |
| C18:1w9c | 0.26 | 0.51 |
| PUFA | | |
| C18:2 | | 11.20 |
| C18:2w6,9, all cis | 9.88 | |
| C20:4w6,6,9,12,15 all cis | | |
| C20:5w3 (EPA) | 0.67 | 2.03 |
| Hydroxy | | |
| C16:0 2-OH | 3.82 | 0.17 |
| C17:1 2-OH | 11.88 | 5.56 |
| O-Alkylglycerols (OAG) | | |
| C14:0 | | |
| C15:0 | 0.51 | |
| C16:0 | | 21.94 |
| C16:1 | | |
| Total | 71.39 | 75.44 |
| Branched-chain | | |
| iso-C13:0 | 0.32 | 0.14 |
| iso-C14:0 | 0.12 | |
| iso-C15:0 | 11.68 | 8.94 |
| iso-C16:0 | 1.51 | 0.06 |
| iso-C17:0 | 12.23 | 7.05 |
| Branched-chain hydroxy | | |
| iso-C17:0 2-OH | 2.76 | 0.79 |
| Branched-chain OAG | | |
| iso-C15:0 OAG | | 7.59 |
| Total | 28.61 | 24.56 |

TABLE 9

Distribution of fatty acids among *Nann.ocystineae*: EPA was found in *Enhygromyxa salina*

| | Hoch | Htep | Esal | Ppac | Kfla | Nexe | Npus |
|---|---|---|---|---|---|---|---|
| Straight-chain | | | | | | | |
| C13:0 | | | | | | 0.56 | |
| C14:0 | 0.18 | | 0.79 | 0.41 | | 17.33 | 11.14 |
| C14:1w5c | | | 0.68 | 0.64 | | | |
| C15:0 | 0.63 | | 0.45 | 0.18 | 0.35 | 2.37 | |
| C15:1 | | | | | | 2.12 | |
| C16:0 | 18.41 | 2.89 | 10.69 | 6.67 | 2.81 | 12.01 | 2.22 |
| C16:1w5c | 3.57 | | 0.96 | 0.65 | 0.37 | 22.01 | 14.81 |
| C16:1w7c | 8.84 | | 42.24 | 30.13 | | | |
| C16:1w9c | | 3.27 | | 22.41 | 0.82 | 6.68 | |
| C16:1w11c | | | | | | | 1.11 |
| C17:0 | 1.81 | | 0.39 | 0.20 | 0.73 | | |
| C17:1w7c | 0.52 | | 0.53 | 0.32 | | | |
| C18:0 | 4.81 | 2.23 | 5.88 | 3.19 | 0.76 | 7.75 | 1.23 |
| C18:1 | 2.23 | | | | | | |
| C18:1w9c | 0.72 | 2.24 | 29.09 | 23.59 | | | |
| PUFA | | | | | | | |
| C20:4w6, 9, 12, 15 all cis | | | 0.91 | 2.55 | | | |
| C20:5w3 (EPA) | | | 1.44 | | | | |
| O-Alkylglycerols (OAG) | | | | | | | |
| C14:0 | | | | | | 0.31 | |
| C15:0 | 0.72 | | 0.33 | | | 0.49 | |
| C16:0 | 6.98 | 0.18 | 1.48 | | | 0.67 | |
| C16:1 | 0.20 | 2.93 | | | | 6.55 | |
| Total | 49.62 | 13.73 | 95.87 | 90.93 | 13.86 | 70.84 | 30.51 |
| Branched-chain | | | | | | | |
| iso-C14:0 | | | | | | 0.15 | |
| iso-C15:0 | 2.38 | 17.86 | 0.57 | 2.76 | 1.72 | 8.69 | 14.83 |
| iso-C16:0 | 25.45 | 14.02 | 1.20 | 2.46 | 34.14 | | 0.70 |
| iso-C16:1 | 8.94 | 18.69 | | | 27.85 | | |
| iso-C17:0 | 5.00 | 8.76 | 0.66 | 0.46 | 12.63 | 14.74 | 34.44 |
| iso-C17:1w5c | | 0.76 | | | | | 4.21 |
| iso-C17:1w11c | | | | | | 3.53 | 11.37 |
| iso-C18:0 | 0.11 | | | | 0.45 | | |
| anteiso-C17:0 | 2.01 | 3.14 | | | 1.81 | | |
| Branched-chain OAG | | | | | | | |
| iso-C15:0 | 4.84 | 23.05 | 1.69 | 3.39 | 4.61 | | 0.74 |
| Branched-chain DMA | | | | | | | |
| iso-C15:0 | 1.65 | | | 2.79 | | 2.20 | 3.24 |
| Total | 50.38 | 86.27 | 4.13 | 9.07 | 86.14 | 29.16 | 69.52 |

Legend:
Hoch: *Heliangium ochraceum*,
Htep: *Heliangium tepidum*,
Esal: *Enhygromyxa salina*,
Ppac: *Plesiocystis pacifica*,
Kfla: *Kofleria flava*,
Nexe: *Nannocystis exedens*,
Npus: *Nannocystis pusilla*.

Example 6: Phylogeneny of Myxobacteria in Relation to Fatty Acid Production, with Special Emphasis on Omega-3 PUFAS Myxobacteria are currently divided into six families, twenty genera and 46 species, which can be segregated based on morphological, biochemical and physiological character. This taxonomy was also reflected by molecular phylogenetic studies, based on similarity analyses of their 16S rDNA, revealing Myxobacteria as a monophyletic group [Velicer G, Hillesland K (2008) In Myxobacteria: multicellularity and differentiation (Whitworth D, ed), pp. 17-40. ASM Press:Washington D.C.; Spröer C et al. (1999) Int J Syst Bacteriol 49, 1255-1262; Garcia R O et al. (2009) Int J Syst Evol Microbiol 59:1524-1530].

Following the surprising discovery that the members of the novel, undescribed genus *Aetherobacter* were capable of producing omega-3 PUFAs as major fatty acids in their biomass, a panel of representative strains of class Myxobacteria were selected to study their fatty acid profiles in order to investigate the distribution of PUFAs and other fatty acids and in particular, the specificity of the overproduction of PUFAs by the novel genus *Aetherobacter*. Preferably, the type strains of culturable species, including terrestrial as well as marine species, were selected.

Reference 16S rDNA gene sequences used in this study were downloaded from GenBank. Corrected sequences of the type and novel strains were also included (table 1). Sequence alignments were created using the software ClustalW version 2.0. [Larkin et al. (2007) Bioinformatics Applications Note 23(21): 2947-2948].

Distance matrices between sequences were calculated using the Jukes-Cantor model [Jukes T H, Cantor C R (1969) Evolution of protein molecules. pp. 21-123 in H N Munro (ed) Mammalian protein metabolism. New York: Academic Press]. From the distance matrices, a neighbour-joining tree was constructed as described by Saitou N & Nei M (1987) Mol Biol Evol 4:406-425. A bootstrap of 1000 replicates was designed [Felsenstein J (1985) Evolution 39:783-791], and a consensus tree was performed using the Geneious tree builder. All these programs are packed in the Geneious Pro 4.7.6 software, available from Geneious (Auckland, New Zealand).

Figure 5:
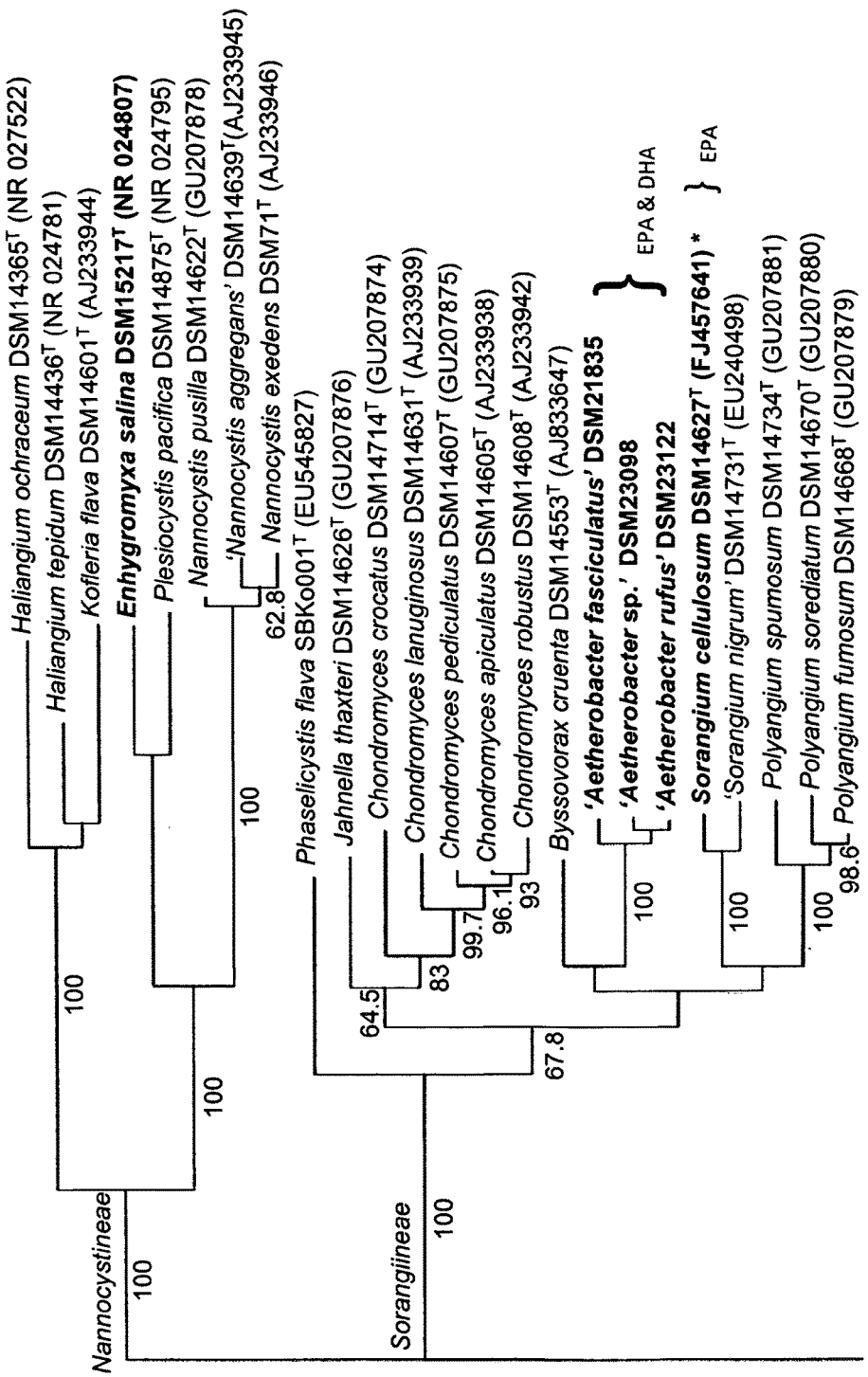
FIG. 5: Neighbor-joining tree based on myxobacterial 16S rDNA gene sequence, and showing the phylogenetic position of EPA and DHA producing strains (bold). The numbers at branchpoints indicate the level of bootstrap support, based on 1,000 resamplings. Only values greater than 60 are shown. Bar, 0.05 substitutions per nucleotide position. Legend*: The type strain of *Sorangium cellulosum* in this tree represents only the possibility for the production of omega-3 fatty acids in the genus *Sorangium*. In other strains of *Sorangium cellulosum* as exemplified by SBSo021 and SBSo024 (DNA sequences not included in this tree), the production of EPA was already discovered, but the type strain itself was devoid of omega-3 PUFA production.

Genomic DNA was extracted from actively growing cultures using the protocol for Gram-negative bacteria of the Qiagen genomic DNA purification kit (Gentra Systems Inc., Minneapolis, USA). Only strains with gaps and 'N' sequences were prepared for repeated 16S rDNA gene sequencing. All type strains without 16S rDNA gene sequence were also included (FIG. 5). Aliquots of DNA were prepared for PCR using universal primers [Lachnik J et al. (2002) J Clin Microbiol 40:3364-3373]. These primers (forward primer GAGTTTGATCCTGGCTCAGGA; reverse primer AAGGAGGTGATCCAGCCGCA) were also used for sequencing of the PCR products. Additional primers were designed to cover the end sequences of the gene and were also used for further sequencing. Purification of the PCR product was performed using the NucleoSpin kit (Macherey-Nagel, Duren, Germany).

Homology analyses of 16S rDNA sequence data: According to the widely used and well established BLASTn analysis [Zhang Z et al. (2000) J Comput Biol 7:203-214, the newly obtained 16S rDNA sequences of the *Aetherobacter* strains were checked for homology to published sequence data. tables 10-12 show the results of the BLASTn searches for each individual strain. The 16S rDNA sequence of *A. fasciculatus* DSM 21835 showed 96% identity to the cellulose-degrading *Byssovorax* (*Byssophaga*) *cruenta* DSM 14553$^T$ and 95% to *Sorangium* (syn: *Polyangium*) *cellulosum* strains (table 10). Surprisingly, the 16S rDNA sequence of *A. rufus* DSM 23122 and *Aetherobacter* sp. DSM 23098 also showed 96% identity with *Byssovorax cruenta* (table 11) and 95% to *Sorangium cellulosum* strains (table 12).

The above data reveal that as inferred from the homologies of 16S rDNA, the identification of all three *Aetherobacter* strains as members of the *Mycococcales* is further confirmed. The novel bacterial strains are most closely related to members of the family Polyangiaceae, as indicated by homologies to *Byssovorax* (*Byssophaga*) *cruenta* and

Figure 6:
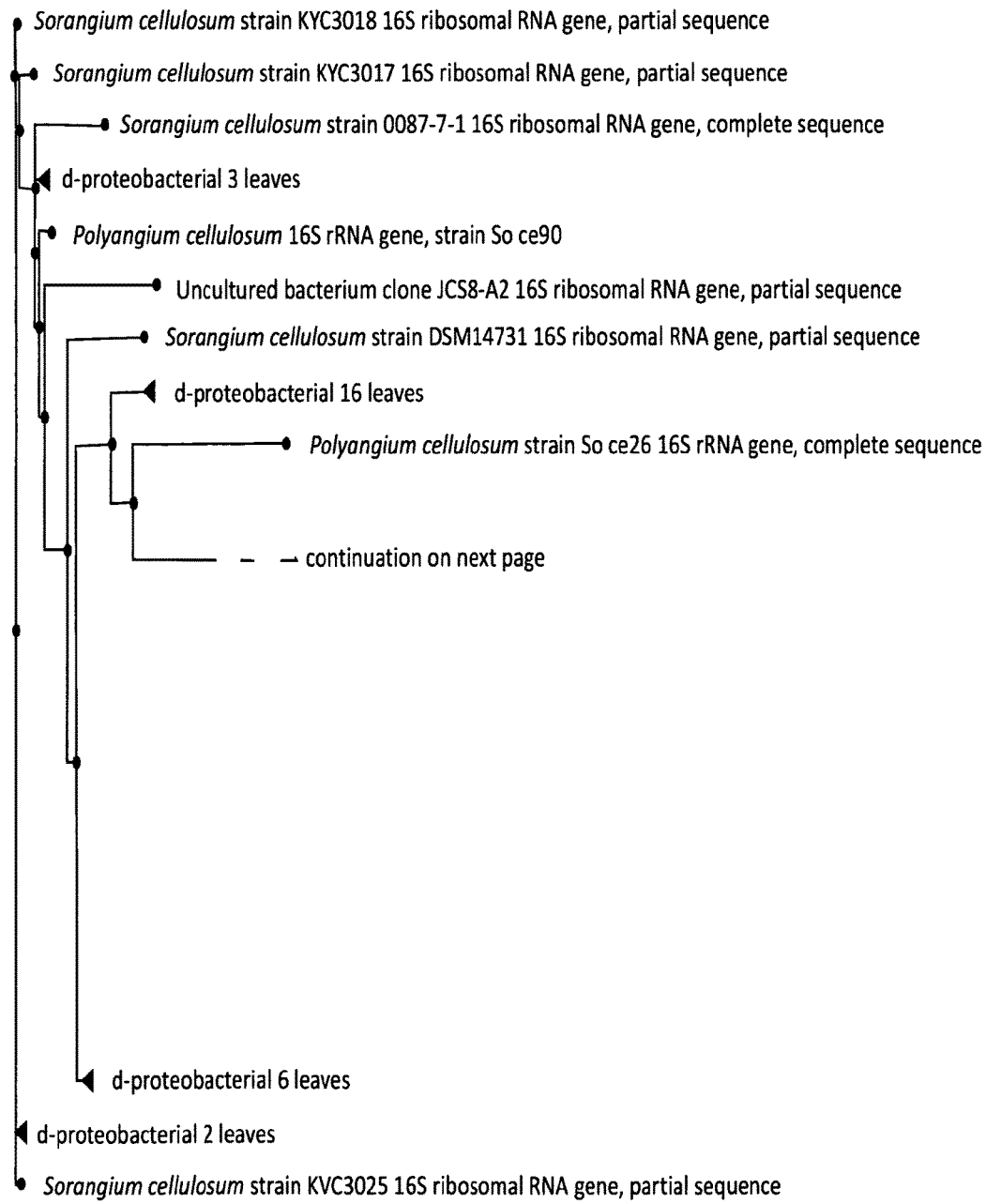
FIG. 6: Neighbor-joining tree generated from NCBI-BLASTn showing the affinities of the 16S rDNA sequences of *Aetherobacter fasciculatus*. DSM 21835 (arrow) to the most homologous 50 representative sequences available in GenBank at Nov. 22, 2009.

*Sorangium* (syn: *Polyangium*) *cellulosum*. The closest similarity (96-98%) were found to bacterial clones which may perhaps represent further hitherto uncultured species of myxobacteria that are more or less immediately allied to the genus *Aetherobacter*. This relationship is illustrated for *Aetherobacter fasciculatus* DSM 21835 in FIG. 6 exemplarily. Nearly identical results were obtained for the other *Aetherobacter* strains.

TABLE 10

BLASTn2.2.22+ homology of 16S rDNA sequence data of *Aetherobacter fasciculatus* DSM 21835, revealing the most similar DNA sequences deposited with GenBank on Nov. 22, 2009.

| Accession | Description | Max score | Total score | Query coverage | E value | Max ident |
|---|---|---|---|---|---|---|
| FN421522 | Uncultured bacterium partial 16S rDNA gene, clone 12_G10 | 2553 | 2553 | 92% | 0.0 | 98% |
| FJ479473 | Uncultured bacterium clone p35k08ok 16S ribosomal DNA gene, partial sequence | 2527 | 2527 | 97% | 0.0 | 96% |
| AJ833647 | *Byssophaga cruenta* partial 16S rDNA gene, strain DSM 14553T | 2488 | 2488 | 98% | 0.0 | 96% |
| AF467674 | *Polyangium cellulosum* strain So9857 16S ribosomal DNA gene, complete sequence | 2475 | 2475 | 100% | 0.0 | 95% |
| FJ457644 | *Sorangium cellulosum* strain KYC3093 16S ribosomal DNA gene, partial sequence | 2464 | 2464 | 99% | 0.0 | 95% |
| FJ457643 | *Sorangium cellulosum* strain KYC3074 16S ribosomal DNA gene, partial sequence | 2462 | 2462 | 99% | 0.0 | 95% |
| AF467672 | *Polyangium cellulosum* strain So9881 16S ribosomal DNA gene, complete sequence | 2460 | 2460 | 99% | 0.0 | 95% |
| AF387629 | *Polyangium cellulosum* strain So ce26 16S ribosomal DNA gene, complete sequence | 2460 | 2460 | 99% | 0.0 | 95% |
| FJ176770 | *Sorangium cellulosum* strain KYC3047 16S ribosomal DNA gene, partial sequence | 2457 | 2457 | 99% | 0.0 | 95% |
| FJ457645 | *Sorangium cellulosum* strain KYC3139 16S ribosomal DNA gene, partial sequence | 2451 | 2451 | 99% | 0.0 | 95% |
| FJ457642 | *Sorangium cellulosum* strain KYC3059 16S ribosomal DNA gene, partial sequence | 2451 | 2451 | 99% | 0.0 | 95% |
| FJ176771 | *Sorangium cellulosum* strain KYC3076 16S ribosomal DNA gene, partial sequence | 2451 | 2451 | 99% | 0.0 | 95% |
| AF467675 | *Polyangium cellulosum* strain So9735-22 16S ribosomal DNA gene, complete sequence | 2449 | 2449 | 99% | 0.0 | 95% |
| AM746676 | *Sorangium cellulosum* 'So ce 56' complete genome | 2447 | 9786 | 100% | 0.0 | 95% |

TABLE 11

BLASTn2.2.22+ homology of 16S rDNA sequence data of *Aetherobacter rufus* DSM 23122 revealing the most similar DNA sequences deposited with GenBank on Nov. 22, 2009.

| Accession | Description | Max score | Total score | Query coverage | E value | Max ident |
|---|---|---|---|---|---|---|
| FN421522 | Uncultured bacterium partial 16S rDNA gene, clone 12_G10 | 2595 | 2595 | 92% | 0.0 | 99% |
| FJ479473 | Uncultured bacterium clone p35k08ok 16S ribosomal DNA gene, partial sequence | 2558 | 2558 | 97% | 0.0 | 97% |
| AJ833647 | *Byssophaga cruenta* partial 16S rDNA gene, strain DSM 14553T | 2514 | 2514 | 98% | 0.0 | 96% |
| AF467674 | *Polyangium cellulosum* strain So9857 16S ribosomal DNA gene, complete sequence | 2497 | 2497 | 99% | 0.0 | 95% |
| AM746676 | *Sorangium cellulosum* 'So ce 56' complete genome | 2490 | 9956 | 99% | 0.0 | 95% |
| AF467672 | *Polyangium cellulosum* strain So9881 16S ribosomal DNA gene, complete sequence | 2481 | 2481 | 99% | 0.0 | 95% |
| AF387629 | *Polyangium cellulosum* strain So ce26 16S ribosomal DNA gene, complete sequence | 2481 | 2481 | 99% | 0.0 | 95% |
| FJ457644 | *Sorangium cellulosum* strain KYC3093 16S ribosomal DNA gene, partial sequence | 2479 | 2479 | 99% | 0.0 | 95% |
| FJ457643 | *Sorangium cellulosum* strain KYC3074 16S ribosomal DNA gene, partial sequence | 2477 | 2477 | 99% | 0.0 | 95% |
| FJ176770 | *Sorangium cellulosum* strain KYC3047 16S ribosomal DNA gene, partial sequence | 2471 | 2471 | 99% | 0.0 | 95% |
| DQ083111 | Uncultured bacterium clone S137 16S ribosomal DNA gene, partial sequence | 2471 | 2471 | 97% | 0.0 | 96% |
| FJ457646 | *Sorangium cellulosum* strain KYC3466 16S ribosomal DNA gene, partial sequence | 2468 | 2468 | 99% | 0.0 | 95% |
| FJ457645 | *Sorangium cellulosum* strain KYC3139 16S ribosomal DNA gene, partial sequence | 2468 | 2468 | 99% | 0.0 | 95% |
| FJ457642 | *Sorangium cellulosum* strain KYC3059 16S ribosomal DNA gene, partial sequence | 2466 | 2466 | 99% | 0.0 | 95% |

TABLE 12

BLASTn2.2.22+ homology of 16S rDNA sequence data of *Aetherobacter* sp. DSM 23098 revealing the most similar DNA sequences deposited with GenBank on Nov. 22, 2009.

| Accession | Description | Max score | Total score | Query coverage | E value | Max ident |
|---|---|---|---|---|---|---|
| FN421522 | Uncultured bacterium partial 16S rDNA gene, clone 12_G10 | 2566 | 2566 | 92% | 0.0 | 98% |
| FJ479473 | Uncultured bacterium clone p35k08ok 16S ribosomal DNA gene, partial sequence | 2534 | 2534 | 97% | 0.0 | 96% |
| AJ833647 | *Byssophaga cruenta* partial 16S rDNA gene, strain DSM 14553T | 2490 | 2490 | 98% | 0.0 | 96% |
| AF467674 | *Polyangium cellulosum* strain So9857 16S ribosomal DNA gene, complete sequence | 2481 | 2481 | 99% | 0.0 | 95% |
| AF387629 | *Polyangium cellulosum* strain So ce26 16S ribosomal DNA gene, complete sequence | 2470 | 2470 | 99% | 0.0 | 95% |
| FJ457644 | *Sorangium cellulosum* strain KYC3093 16S ribosomal DNA gene, partial sequence | 2466 | 2466 | 99% | 0.0 | 95% |
| EU881332 | Uncultured bacterium clone KMS200711-118 16S ribosomal DNA gene, partial sequence | 2466 | 2466 | 98% | 0.0 | 95% |
| FJ457643 | *Sorangium cellulosum* strain KYC3074 16S ribosomal DNA gene, partial sequence | 2464 | 2464 | 99% | 0.0 | 95% |
| AF467672 | *Polyangium cellulosum* strain So9881 16S ribosomal DNA gene, complete sequence | 2464 | 2464 | 99% | 0.0 | 95% |
| FJ176770 | *Sorangium cellulosum* strain KYC3047 16S ribosomal DNA gene, partial sequence | 2459 | 2459 | 99% | 0.0 | 95% |
| AM746676 | *Sorangium cellulosum* 'So ce 56' complete genome | 2459 | 9830 | 99% | 0.0 | 95% |
| FJ457645 | *Sorangium cellulosum* strain KYC3139 16S ribosomal DNA gene, partial sequence | 2455 | 2455 | 99% | 0.0 | 95% |
| FJ457641 | *Sorangium cellulosum* strain DSM14627 16S ribosomal DNA gene, partial sequence | 2455 | 2455 | 99% | 0.0 | 95% |
| EU242519 | *Sorangium cellulosum* strain KYC3025 16S ribosomal DNA gene, partial sequence | 2455 | 2455 | 99% | 0.0 | 95% |

Example 7: Outgroup Organisms 16S rDNA sequence of *Flexibacter flexilis* (Gen Bank Acc. no AB078050), derived from strain IFO 15060 showed 76% similarity to that of *Aerherobacter fasciculatus*, and other *Aetherobacter* species, while the 16S rDNA sequence of *Herpetosiphon geysericola* (GenBank Acc. No. AF039293) showed 75% similarity upon a BLAST comparison, determined with the same procedure outlined in the above examples.

These two species are gliding bacteria and belong to the delta subgroup of proteobacteria; they are deemed to be closely related to the myxobacteria but do not produce fruiting bodies and omega-3 PUFAs.

---

The invention claimed is:

1. A method for the production of omega-3 polyunsaturated fatty acids which comprises:
   (a) preparing a vegetative inoculum of cells of an *Aetherobacter* strain that produces one or more omega-3 polyunsaturated fatty acids, wherein the *Aetherobacter* strain has a 16s rDNA sequence that is at least 97% identical to the 16s rDNA sequence set forth in SEQ ID NO: 1, 2 or 4;
   (b) transferring the inoculum of step (a) to an aqueous nutrient medium and culturing the cells of said *Aetherobacter* strain under submerged aerobic conditions; and
   (c) isolating one or more omega-3 polyunsaturated fatty acids from the cells cultured in step (b), wherein isolating comprises the steps of drying the cells, extracting the dried cells and purifying the one or more omega-3 polyunsaturated fatty acids.

2. The method according to claim 1, wherein the *Aetherobacter* strain has an omega-3 polyunsaturated fatty acid content of at least 15% by weight of total cellular fatty acid content.

3. The method according to claim 1, wherein the *Aetherobacter* strain is an *Aetherobacter fasciculatus* strain, which is aerobic, facultatively aerobic, or chemo heterotrophic, and comprises a 16S rDNA sequence that is about 96% identical with the *Byssovorax* (*Byssophaga*) *cruenta* DSM 14553$^T$ 16 S rDNA sequence as set forth in SEQ ID NO:3.

4. The method of claim 3, wherein the *Aetherobacter* strain has an omega-3 polyunsaturated fatty acid content of at least 15% by weight of total cellular fatty acid content.

5. The method according to claim 1, wherein the *Aetherobacter* strain is strain *Aetherobacter fasciculatus* DSM 21835.

6. The method according claim 1, wherein the *Aetherobacter* strain is strain *Aetherobacter rufus* DSM 23122.

7. The method according claim 1, wherein the *Aetherobacter* strain is classified as *Aetherobacter* sp. strain DSM 23098.

8. The method according to claim 1, wherein the omega-3 polyunsaturated fatty acids are selected from (a) eicosapentaenoic acid (EPA), (b) docosahexaenoic acid (DHA) and (c) mixtures of EPA and DHA.

9. The method according to claim 8, wherein the *Aetherobacter* strain produces EPA at least at an amount of 0.50 µg per 9.25 mg dry cell weight and DHA at least at an amount of 0.69 µg per 9.25 mg dry cell weight.

10. The method according claim 1, further comprising: isolating an individual omega-3 polyunsaturated fatty acid from the culture.

\* \* \* \* \*

SEQUENCE LISTING

```
<160> NUMBER OF SEQ ID NOS: 4

<210> SEQ ID NO 1
<211> LENGTH: 1548
<212> TYPE: DNA
<213> ORGANISM: Aetherobacter fasciculatus
<220> FEATURE:
<221> NAME/KEY: source
<222> LOCATION: 1..1548
<223> OTHER INFORMATION: /mol_type="DNA"
      /organism="Aetherobacter fasciculatus"
<220> FEATURE:
<221> NAME/KEY: gene
<222> LOCATION: 1..1548
<223> OTHER INFORMATION: /function="16S rDNA"

<400> SEQUENCE: 1
agtttgatcc tggctcagaa cgaacgttag cggcgcgctt aacacatgca agtcgagcga        60
gaaaggggca accccggtaa agcggcgcac gggtgagtaa cacgtaggta atctaccccc       120
aggtggtgga taaccttccg aaaggaaggc taatacagca tgggaccacg acctcgcaag       180
gggttgaggt gaaagttggc ctcttcatga aagccaacgc caggggatga gcctgcggcc       240
catcagctag ttggtagggt aatggcctac caaggcaaag acgggtagct ggtctgagag       300
gatgatcagc cacactggaa ctgagacacg gtccagactc ctacgggagg cagcagtgg       360 ggaatcttgc gcaatgggcg aaagcctgac gcagcgacgc cgcgtgagtg atgaaggccc       420
```

```
tcgggttgta aagctctgtg gagggggacg aataagcgtt ggttaatatc cagcgtgatg      480
acggtaccct tttagcaagc accggctaac tctgtgccag cagccgcggt aagacagagg      540
gtggcaaacg ttgttcggaa ttactgggcg taaagcgcgt gtaggctgct tcgcaagtcg      600
gatgtgaaaa gccctgggc tcaacccagg aagtgcattc gaaactgcaa agctggagtc       660
ctggagagga aggcggaatt ctcggtgtag aggtgaaatt cgtagatatc gagaggaaca      720
ccggtggcga aggcggcctt ctggacagtg actgacgctg agacgcgaaa gcgtggggag      780
caaacaggat tagataccct ggtagtccac gccgtaaacg atgggtgcta ggtgttgcgg      840
gctttgaccc ctgcagtgcc gtagctaacg cattaagcac cccgcctggg gagtacggcc      900
gcaaggctaa aactcaaagg aattgacggg ggcccgcaca agcggtggag catgcggttc      960
aattcgacgc aacgcgcaga accttacctg gctagaaaa tgcaaggacc tggtcgaaag     1020 atcgggtgc tcttcggaga acttgtagtt aggtgctgca tggctgtcgt cagctcgtgt      1080
cgtgagatgt tgggttaagt cccgcaacga gcgcaacccc tgtcgttagt tgccatcagt     1140
tcggctgggc actctagcga gactgccgat ctttaaatcg gaggaaggtg gggatgacgt     1200
caagtcatca tggccttat gtccagggct acacgcgtgc tacaatggtc ggtacaaacg      1260
gttgcgaagt cgcgaggcga agctaatccg aaaaaaccgg cctcagtacg ataagagtc      1320 tgcaactcga ctctttgaag tcggaatcgc tagtaatccc tgatcagcag gcaggggtga      1380
atacgttccc gggccttgta cacaccgccc gtcacaccat gggagtcgat tgctccagaa      1440
gtggctgcgc aacccgcaa gggaggcagg cccccaagga gtggttggta actggggtga       1500
agtcgtaaca aggtagccgt aggggaacct gcggctggat cacctcct                  1548

<210> SEQ ID NO 2
<211> LENGTH: 1551
<212> TYPE: DNA
<213> ORGANISM: Aetherobacter rufus
<220> FEATURE:
<221> NAME/KEY: source
<222> LOCATION: 1..1551
<223> OTHER INFORMATION: /mol_type="DNA"
      /organism="Aetherobacter rufus"
<220> FEATURE:
<221> NAME/KEY: gene
<222> LOCATION: 1..1551
<223> OTHER INFORMATION: /function="16S rDNA"

<400> SEQUENCE: 2
tagagtttga tcctggctca gaacgaacgt tagcggcgcg cttaacacat gcaagtcgag       60
cgagaaaggg gcaaccccgg taaagcggcg cacgggtgag taacacgtag gtaatctacc      120
cccaggtggt ggataaccct ccgaaaggaa ggctaataca gcatgggacc acggctccga      180
aaggagttga ggtgaaagtc ggcctcttca tgaaagccga cgccagggga tgagcctgcg      240
gcccatcagc tagttggtag ggtaatggcc taccaaggcg aagacgggta gctggtctga      300
gaggatgatc agccacactg gaactgagac acggtccaga ctcctacggg aggcagcagt      360
ggggaatctt gcgcaatggg cgaaagcctg acgcagcgac gccgcgtgag tgatgaaggc      420
cctcgggttg taaagctctg tggagggga cgaataagcg ttggttaata tccagcgtga       480
tgacggtacc ctttttagcaa gcaccggcta actctgtgcc agcagccgcg gtaagacaga      540
gggtgcaaac gttgttcgga attactgggc gtaaagcgcg tgtaggctgc ttcgcaagtc      600
ggatgtgaaa gccctgggct caacccagga agtgcattcg aaactgcaga gctggagtcc      660
tggagaggaa ggcggaattc tcggtgtaga ggtgaaattc gtagatatcg agaggaacac      720
```

| | |
|---|---|
| cggtggcgaa ggcggccttc tggacagtga ctgacgctga gacgcgaaag cgtggggagc | 780 |
| aaacaggatt agatacctg gtagtccacg ccgtaaacga tgggtgctag gtgttgcggg | 840 |
| ctttgacccc tgcagtgccg tagctaacgc attaagcacc ccgcctgggg agtacggccg | 900 |
| caaggctaaa actcaaagga attgacgggg cccgcacaa gcggtggagc atgcgggttc | 960 |
| aattcgacgc aacgcgcaga accttacctg gctagaaaa tgcaaggacc tgggtcgaaa | 1020 |
| gatcggggtg ctcttcggag agcttgtagt taggtgctgc atggctgtcg tcagctcgtg | 1080 |
| tcgtgagatg ttgggttaag tcccgcaacg agcgcaaccc ctgtcgttag ttgccatcag | 1140 |
| ttcggctggg cactctagcg agactgccga tctttaaatc ggaggaaggt ggggatgacg | 1200 |
| tcaagtcatc atggccctta tgtccagggc tacacgcgtg ctacaatggt cggtacaaac | 1260 |
| ggttgcgaag tcgcgaggcg aagctaatcc gaaaaaaccg gcctcagtac ggataagagt | 1320 |
| ctgcaactcg actctttgaa gtcggaatcg ctagtaatcc ctgatcagca ggcagggtg | 1380 |
| aatacgttcc cgggccttgt acacaccgcc cgtcacacca tgggagtcga ttgctccaga | 1440 |
| agtggctgcg ccaacccgca agggaggcag ccccccaagg agtggttggt aactggggtg | 1500 |
| aagtcgtaac aaggtagccg taggggaacc tgcggctgga tcacctcctt a | 1551 |

<210> SEQ ID NO 3
<211> LENGTH: 1529
<212> TYPE: DNA
<213> ORGANISM: Byssovorax cruenta
<220> FEATURE:
<221> NAME/KEY: source
<222> LOCATION: 1..1529
<223> OTHER INFORMATION: /mol_type="DNA"
    /organism="Byssovorax cruenta"
<220> FEATURE:
<221> NAME/KEY: gene
<222> LOCATION: 1..1529
<223> OTHER INFORMATION: /function="16S rDNA"

<400> SEQUENCE: 3

| | |
|---|---|
| tgatcctggc tcagaacgaa cgttagcggc gcgcctaaca catgcaagtc gagcgagaaa | 60 |
| ggggaaaccc cggtaaagcg gcgcacgggt gagtaacacg taggtaatct accccccaggt | 120 |
| ggtggataac cttccgaaag gagggctaat acagcatgag accacgtttc cgcaagggag | 180 |
| tgaggtcaaa gccggcctct tcacgaaagc tggcgccagg ggatgagcct gcggcccatc | 240 |
| acggtagttg gtagggtaat ggcctaccaa gccaaagacg ggtagctggt ctgagaggat | 300 |
| gatcagccac actggaactg agacacggtc cagactccta cgggaggcag cagtggggaa | 360 |
| tcttgcgcaa tgggcgaaag cctgacgcag cgacgccgcg tgagtgatga aggccttcgg | 420 |
| gttgtaaagc tctgtgggga gggacgaata agtgttggct aacatccagc atgatgacgg | 480 |
| tacctctttta gcaagcaccg gctaactctg tgccagcagc cgcggtaaga cagagggtgc | 540 |
| aaacgttgtt cggaattact gggcgtaaag cgcgtgtagg ctgcttcgaa agtcggatgt | 600 |
| gaaagccctg ggctcaacct aggaagtgca ttcgaaactt cggagcttga gttctgagga | 660 |
| ggaaggcgga attctcggtg tagaggtgaa attcgtagat atcgagagga acaccggtgg | 720 |
| cgaaggcggc cttctggaca gatactgacg ctgagacgcg aaagcgtggg gagcaaacag | 780 |
| gattagatac cctggtagtc cacgccgtaa acgatgggtg ctaggtgtcg cgggctttga | 840 |
| ccctgcgt gccgtagcta acgcattaag caccccgcct ggggagtacg ccgcaaggc | 900 |
| taaaactcaa aggaattgac gggggcccgc acaagcggtg gagcatgtgg ttcaattcga | 960 |
| cgcaacgcgc agaaccttac ctgggctaga aaatgcaggg acctggctga aaagtcgggg | 1020 |

```
tgctcttcgg agaacctgta gttaggtgct gcatggctgt cgtcagctcg tgtcgtgaga      1080
tgttgggtta agtcccgcaa cgagcgcaac ccttgtcgtt agttgccagc ggttcggccg      1140
ggcactctag cgagactgcc gatattcaaa tcggaggaag gtggggatga cgtcaagtca      1200
tcatggccct tatgtccagg gctacacacg tgctacaatg gtcggtacaa acggttgcga      1260
actcgcgagg ggaagctaat ccgaaaaaac cgacctcagt acggataaga gtctgcaact      1320
cgactctttg aagtcggaat cgctagtaat ccctgatcag caggcagggg tgaatacgtt      1380
cccgggcctt gtacacaccg cccgtcacac catgggagtc gattgctcca gaagtggctg      1440
cgccaacccg caagggaggc aggcccccaa ggagtggttg gtaactgggg tgaagtcgta      1500
acaaggtagc cgtaggggaa cctgcggct                                        1529

<210> SEQ ID NO 4
<211> LENGTH: 1548
<212> TYPE: DNA
<213> ORGANISM: Aetherobacter
<220> FEATURE:
<221> NAME/KEY: source
<222> LOCATION: 1..1548
<223> OTHER INFORMATION: /mol_type="DNA"
     /organism="Aetherobacter"
<220> FEATURE:
<221> NAME/KEY: gene
<222> LOCATION: 1..1548
<223> OTHER INFORMATION: /function="16S rDNA"

<400> SEQUENCE: 4
tgagtttgat cctggctcag gacgaacgtt agcggcgcgc ttaacacatg caagtcgagc        60
gagaaagggg caaccccggt aaagcggcgc acgggtgagt aacacgtagg taatctaccc       120
ccaggtggtg gataaccttc cgaaaggaag gctaatacag catgggacca cggcctcgca       180
agaggttgag gtgaaagttg gcctcttcat gaaagccaac gccaggggat gagcctgcgg       240
cccatcagct agttggtagg gtaatggcct accaaggcaa agacgggtag ctggtctgag       300
aggatgatca gccacactgg aactgagaca cggtccagac tcctacggga ggcagcagtg       360
gggaatcttg cgcaatgggc gaaagcctga cgcagcgacg ccgcgtgagt gatgaaggcc       420
ctcgggttgt aaagctctgt ggaggggggac gaataagcgt tggttaatat ccagcgtgat      480
gacggtaccc ttttagcaag caccggctaa ctctgtgcca gcagccgcgg taagacagag       540
ggtgcaaacg ttgttcggaa ttactgggcg taaagcgcgt gtaggctgct cgcaagtcg        600 gatgtgaaag ccctgggctc aacccaggaa gtgcattcga aactgcaaag ctggagtcct       660
ggagaggaag gcggaattct cggtgtagag gtgaaattcg tagatatcga gaggaacacc       720
ggtggcgaag gcggccttct ggacagtgac tgacgctgag acgcgaaagc gtggggagca       780
aacaggatta gataccctgg tagtccacgc cgtaaacgat gggtgctagg tgttgcgggc       840 tttgaccccct gcagtgccgt agctaacgca ttaagcaccc cgcctgggga gtacggccgc      900
aaggctaaaa ctcaaaggaa ttgacggggg cccgcacaag cggtggagca tgcggttcaa       960
ttcgacgcaa cgcgcagaac cttacctggg ctagaaaatg caaggacctg tcgaaagat       1020 cggggtgctc ttcggagagc ttgtagttag gtgctgcatg gctgtcgtca gctcgtgtcg      1080
tgagatgttg ggttaagtcc cgcaacgagc gcaacccctg tcgttagttg ccatcagttc      1140
ggctgggcac tctagcgaga ctgccgatct ttaaatcgga ggaaggtggg gatgacgtca      1200
agtcatcatg gcccttatgt ccagggctac acgcgtgcta caatggtcgg tacaaacggt     1260
tgcgaagtcg cgaggcgaag ctaatccgaa aaaccggcc tcagtacgga taagagtctg      1320
```

```
caactcgact ctttgaagtc ggaatcgcta gtaatccctg atcagcaggc aggggtgaat    1380
acgttcccgg gccttgtaca caccgcccgt cacaccatgg gagtcgattg ctccagaagt    1440
ggctgcgcca acccgcaagg gaggcaggcc cccaaggagt ggttggtaac tggggtgaag    1500
tcgtaacaag gtagccgtag gggaacctgc ggctggatca cctcctta              1548
```